US007566449B2

(12) United States Patent
Brooks et al.

(10) Patent No.: US 7,566,449 B2
(45) Date of Patent: *Jul. 28, 2009

(54) METHOD AND COMPOSITION FOR INHIBITION OF ANGIOGENESIS USING ANTAGONISTS BASED ON MMP-9 AND β1 INTEGRINS

(75) Inventors: Peter C. Brooks, West Harrison, NY (US); Dorothy Rodriguez, West Harrison, NY (US)

(73) Assignee: University of Southern California, Los Angeles, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 11/089,999

(22) Filed: Mar. 25, 2005

(65) Prior Publication Data
US 2006/0062777 A1    Mar. 23, 2006

Related U.S. Application Data

(62) Division of application No. 09/615,624, filed on Jul. 13, 2000, now Pat. No. 7,101,975.

(60) Provisional application No. 60/152,495, filed on Sep. 2, 1999, provisional application No. 60/143,581, filed on Jul. 13, 1999.

(51) Int. Cl.
*A61K 39/395* (2006.01)
(52) U.S. Cl. .................................... 424/130.1
(58) Field of Classification Search ............... 530/387.1; 424/130.1
See application file for complete search history.

(56) References Cited

U.S. PATENT DOCUMENTS

| | | | | |
|---|---|---|---|---|
| 5,320,970 | A | 6/1994 | Eyre | |
| 5,530,101 | A | 6/1996 | Queen et al. | 530/387.3 |
| 5,541,295 | A | 7/1996 | Barrach et al. | 530/388.1 |
| 5,693,762 | A | 12/1997 | Queen et al. | |
| 5,763,272 | A | 6/1998 | Naser et al. | 435/325 |
| 5,972,623 | A | 10/1999 | Krane et al. | 435/7.1 |
| 6,030,792 | A | 2/2000 | Otterness et al. | 435/7.1 |
| 6,132,976 | A | 10/2000 | Poole et al. | 435/7.1 |
| 7,101,975 | B1 * | 9/2006 | Brooks et al. | 530/387.1 |

FOREIGN PATENT DOCUMENTS

| | | |
|---|---|---|
| EP | 0 510 949 | 10/1992 |
| EP | 0 921 395 | 6/1999 |
| EP | 0 992 586 | 4/2000 |
| WO | 9414070 | 6/1994 |
| WO | 9504282 | 2/1995 |
| WO | 9744059 | 11/1997 |
| WO | 9835235 | 8/1998 |
| WO | 9906840 | 2/1999 |

OTHER PUBLICATIONS

Poul et al (Molecular Immunology, 1995, 32(2): 101-116).*
Gura (Science, 1997, 278:1041-1042.).*
Tockman et al (Cancer Res., 1992, 52:2711s-2718s).*
Timpl, R., "Antibodies to Collagens and Precollagens", Mtehods in Enzymology, 82 Pt A:472-498 (1982).
Jellinek, et al., "Inhibition of Receptor Binding by High-Affinity RNA Ligands to Vascular Endothelial Growth Factor", Biochemistry, 33 (34):10450-10456 (1994).
Tuerk, C., et al., "Systematic Evolution of Ligands by Exponential Enrichment", RNA Ligands to Bacteriophage T4 DNA Polymerase, Science 249, (Aug. 3, 1990) pp. 505-510.
Ecker, D., et al., Rational Screening of Oligonucleotide Combinatorial Libraries for Drug Discovery, Nucleic Acids Research, vol. 21, No. 8, pp. 1853-1856, (1993).
Wick, G., et al., "Characterization of Antibodies to Basement Membrane (Type IV) Collagen in Immunohistological Studies", Immunobiology, vol. 156, pp. 371-381 (1979).
Bellon, G, "Quantification and Specific Detection of Collagenous Proteins Using an Enzyme-Linked Immunosorbent Assay and an Immunoblotting for Cyanogen Bromide Peptides", Analytical Biochemistry, 1985, vol. 150, pp. 188-202.
Brooks, et al., "Antiintegrin αvβ3 Blocks Human Breast Cancer Growth and Angiogenesis in Human Skin", J. Clin. Invest. Oct. 1995, vol. 96, pp. 1815-1822.
Petitclerc, et al., "Integrin Alpha V Beta 3 Promotes M21 Melanoma Growth in Human Skin By Regulating Tumor Cell Survival", Cancer Research 59:2724-2730, Jun. 1, 1999.
Tennant, et al., "Angiogenesis Inhibitors" Current Oncology Report 2:11-16, Jan. 2000.
Brooks, et al., "Localization of Matrix Metalloproteinase MMP-2 to The Surface of Invasive Cells by Interaction With Integrin Alpha v Beta 3", Cell 85: 683-693, May 31, 1996.
Borza, Dorin-Bogdan, et al., "*Identification of Multiple Cryptic Epitopes on the NC1 Domain of the a3(IV) Collagen Chain*," The Journal of Biological Chemistry, vol. 275, No. 8, Feb. 25, 2000, pp. 6030-6037.
David, Michelle, et al., "*Hydrophobic Amino Acid Residues Are Critical for the Immunodominant Epitope of the Goodpasture Autoantigen*," The Journal of Biological Chemistry, vol. 276, No. 9, 2001, pp. 6370-6377.

(Continued)

*Primary Examiner*—Sean E Aeder
(74) *Attorney, Agent, or Firm*—Hogan & Hartson LLP

(57) ABSTRACT

Antagonists for modifying protein-protein interactions involving certain amino acid sequences within MMP-9 and/or β1 integrins are described. Such antagonists inhibit angiogenesis, tumor growth and disease states. Example antagonists are polypeptide and non-polypeptide molecules, including the novel antibody Mab FM155 and the novel synthetic peptide FRIP-1. Methods for inhibiting angiogenesis and disease states by administering such antagonists are disclosed. Methods for identifying antagonists that modify protein-protein interactions involving certain amino acid sequences within MMP-9 and/or β1 integrins are also described.

24 Claims, 13 Drawing Sheets

OTHER PUBLICATIONS

Greenspan, Neil S., et al., "*Defining Epitopes: It's Not As Easy As It Seems,*" Nature Biotechnology, vol. 17, Oct. 1999, pp. 936-937.

Kalluri, Raghu, et al. "*Specificity of Circulating and Tissue-Bound Autoantibodies in Goodpasture Syndrome,*" Proceedings of the Association of American Physicians, 1996, pp. 135-139.

Mariuzza, R.A., et al. "*The Structural Basis of Antigen-Antibody Recognition,*" Am. Rev. Biophys., Biophys. Chem. 1987, pp. 139-159.

Nakanishi, Koichi, et al., "*Immunohistochemical Study of a 1-5 Chains of Type IV Collagen in Heredity Nephritis,*" Kidney International, vol. 46, 1994, pp. 1413-1421.

Wheatcroft, A.C., "*Evidence of In Situ Stability of the Type IV Collagen Triple Helix in Human Inflammatory Bowel Disease Using a Denaturation Specific Epitope Antibody,*" Matrix Biology 18, 1999, pp. 361-372.

Yang, Wei-Ping, et al., "*CDR Walking Mutagenesis for the Affinity: Maturation of a Potent Human Anti-HIV-1 Antibody into the Picomolar Range,*" J. Mol. Biol., 1995, 254, pp. 392-403.

Yoshioka, Kazuo, et al., "*Normal Distribution and Abnormalities in X-Linked Alport Syndrome Revealed by Monoclonal Antibody,*" American Journal of Pathology, vol. 144, No. 5, 1994, pp. 986-996.

Xu, Jingson, et al., "*Generation of Monoclonal Antibodies to Cryptic Collagen Sites by Using Subtractive Immunization,*" Hybridoma, vol. 19, Nov. 5, 2000, pp. 375-385.

\* cited by examiner

Reactivity of Hybridoma Conditioned Medium For FRIP-1 Peptide

| Hybridoma Clone Name | FRIP-1 (O.D 490nm) | AAA (O.D 490nm) |
|---|---|---|
| FM 101 | 0.306 (± 0.041) | 0.275 (± 0.033) |
| FM132 | 0.576 (± 0.022) | 0.037 (± 0.026) |
| FM155 | 0.481 (± 0.063) | 0.055 (± 0.039) |
| FM158 | 0.339 (± 0.039) | 0.178 (± 0.066) |
| FM170 | 0.241 (± 0.037) | 0.201 (± 0.012) |

METHOD AND COMPOSITION FOR INHIBITION OF ANGIOGENESIS USING ANTAGONISTS BASED ON MMP-9 AND β1 INTEGRINS

CROSS REFERENCE TO RELATED APPLICATION

This application is a divisional of U.S. patent application Ser. No. 09/615,624, filed on Jul. 13, 2000 now U.S. Pat. No. 7,101,975, the content of which is incorporated herein by reference in its entirety.

This application claims the benefit under 35 U.S.C. 119(e) of U.S. Application Ser. No. 60/152,495 filed Sep. 2, 1999, and U.S. Ser. No. 60/143,581 filed Jul. 13, 1999, both of which are herein incorporated by reference.

GOVERNMENT SUPPORT

This invention was made with government support under Contract No. R29CA74132 by the National Institutes of Health.

FIELD OF THE INVENTION

The invention relates generally to the field of medicine, and relates specifically to methods and compositions for inhibiting angiogenesis in a tissue or detecting angiogenesis using antagonists of specified sequences found within MMP-9 and/or β1 integrins.

BACKGROUND

Tumor growth and metastasis impacts a large number of people each year. In fact, it is estimated that well over 600,000 new cases of cancer will be diagnosed in the coming year in the United States alone (Varner, J. A., Brooks, P. C., and Cheresh, D. A. (1995) Cell Adh. Commun. 3, 367-374). Numerous studies have suggested that the growth of all solid tumors requires new blood vessel growth for continued expansion of the tumors beyond a minimal size (Varner et al. 1995; Blood, C. H. and Zetter, B. R. (1990) Biochim. Biophys. Acta. 1032:89-118; Weidner, N. et al. (1992) J. Natl. Cancer Inst. 84:1875-1887; Weidner, N. et al. (1991). N. Engl. J. Med. 324:1-7; Brooks, P. C. et al. (1995) J. Clin. Invest. 96:1815-1822; Brooks, P. C. et al. (1994) Cell 79:1157-1164; Brooks, P. C. et al. (1996). Cell 85, 683-693; Brooks, P. C. et al. (1998) Cell 92:391-400. A wide variety of other human diseases also are characterized by unregulated blood vessel development, including ocular diseases such as macular degeneration and diabetic retinopathy. In addition, numerous inflammatory diseases also are associated with uncontrolled neovascularization such as arthritis and psoriasis (Varner et al. 1995).

New blood vessels develop from pre-existing vessels by a physiological process known as angiogenesis (Varner et al. 1995; Blood and Zetter 1990; Weidner et al. 1992). This complex process requires cooperation of a variety of molecules including growth factors, cell adhesion receptors, matrix degrading enzymes and extracellular matrix components (Varner et al. 1995; Blood and Zetter 1990; Weidner et al. 1992). Thus, therapies designed to block angiogenesis may affect the growth of solid tumors. In fact, clear evidence has been provided that blocking tumor neovascularization can inhibit tumor growth in various animal models, and human clinical data is beginning to support this contention as well (Varner, J. A., Brooks, P. C., and Cheresh, D. A. (1995) Cell Adh. Commun. 3, 367-374).

It has also been proposed that inhibition of angiogenesis can be effected by (1) inhibition of release of "angiogenic molecules" such as βFGF (fibroblast growth factor), (2) neutralization of angiogenic molecules, such as by use of anti-βFGF antibodies, and (3) inhibition of endothelial cell response to angiogenic stimuli. This latter strategy has received attention, and Folkman et al., Cancer Biology, 3:89-96 (1992), have described several endothelial cell response inhibitors, including collagenase inhibitors, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like that might be used to inhibit angiogenesis. For additional proposed inhibitors of angiogenesis, see Blood and Zetter 1990; Moses et al. (1990) Science 248:1408-1410; Ingber et al. (1988) Lab. Invest., 59:44-51; and U.S. Pat. Nos. 5,092,885, 5,112,946, 5,192,744, and 5,202,352.

To block angiogenesis, many investigators have also focused on growth factors and cytokines that initiate angiogenesis (Varner et al. 1995; Blood and Zetter 1990; Weidner et al. 1992; Weidner et al. 1991; Brooks et al. 1995; Brooks et al. 1994; Brooks et al. 1997). However, there is a large number of distinct growth factors and cytokines which have the capacity to stimulate angiogenesis. The therapeutic benefit of blocking a single cytokine may have only limited benefit due to this redundancy. Accordingly, what is needed is other anti-angiogenic targets for inhibiting angiogenesis and proteolysis.

SUMMARY

Invasive cells utilize the protein-protein interaction involving enzymes and integrin receptors to localize proteolytic activity to the cell surface, and to promote invasive cell behavior. The present invention provides methods and compositions for inhibiting angiogenesis and tumor growth using antagonists that target cell adhesion and proteolysis of the extracellular matrix (ECM). Specifically, the present invention provides a novel composition and method for inhibiting angiogenesis based on the discovery of a unique mechanism by which invasive cells localize proteolytic activity, which contributes to the cell surface.

One particular aspect of the invention provides compositions for inhibiting angiogenesis antagonists of protein-protein interactions comprising antagonists of cell adhesion and proteolysis of the extracellular matrix (ECM).

Another aspect of this invention provides compositions for inhibiting angiogenesis comprising antagonists that modify protein protein interactions involving certain sequences sequences found within the proteolytic enzyme MMP-9 and/or β1 integrin receptors. Such antagonists may include, but are not limited to, an antibody or functional fragment thereof, that immunoreacts with MMP-9 and the β1 integrin receptor or a polypeptide or peptide with specificity for a complex of MMP-9 and the β1 integrin receptor.

Yet another aspect of the invention involves methods of inhibiting angiogenesis comprising contacting a tissue with antagonists of cell adhesion and proteolysis of the extracellular matrix (ECM), such as, but not limited to an antibody or functional fragment thereof, that immunoreacts with MMP-9 and the β1 integrin receptor or a polypeptide or peptide with specificity for a complex of MMP-9 and the β1 integrin receptor.

Another aspect of the invention also describes methods for inhibiting a disease state or angiogenesis in a tissue. These methods comprise, for example, administering to the tissue a composition comprising an angiogenesis-inhibiting amount of an antagonist of the localization of the proteolytic enzyme MMP-9 to the cell surface. The disease state to which the invention is applied can be tumor growth or metastasis, macular degeneration, psoriasis, restenosis in a tissue, etc.

The tissue to be treated can be any tissue in which inhibition of angiogenesis is desirable, such as diseased tissue where neo-vascularization is occurring. Exemplary tissues include inflamed tissue, solid tumors, metastases, tissues undergoing restenosis, and the like.

Methods also are provided for detecting angiogenesis, tumorous tissue, metastases, and tumor invasion into a tissue by contacting an antagonist of the invention with a tissue.

The invention also provides methods for screening antagonists of the invention.

Throughout the patent specification,

1. FRIP-1 is the synthetic peptide, which has the sequence: SEQUENCE ID NO: 1: CysArgLeuArgSerGlyGluProGln-Cys;

2. AAA is a control peptide, with the sequence: SEQUENCE ID NO: 2: CysArgAlaAlaAlaGlyGluProGln-Cys; and 3. AAAA is a control peptide with the sequence: SEQUENCE ID NO: 3: CysArgAlaAlaAlaAlaGluProGln-Cys.

BRIEF DESCRIPTION OF THE FIGURES

FIG. 6A is the black and white copy of a color photomicrograph shown in FIG. 6b.

FIG. 9: Shows the results of experiments to generate Mabs directed to the synthetic peptide, FRIP-1 (SEQUENCE ID NO:1).

DETAILED DESCRIPTION OF THE INVENTION

Figure 1:
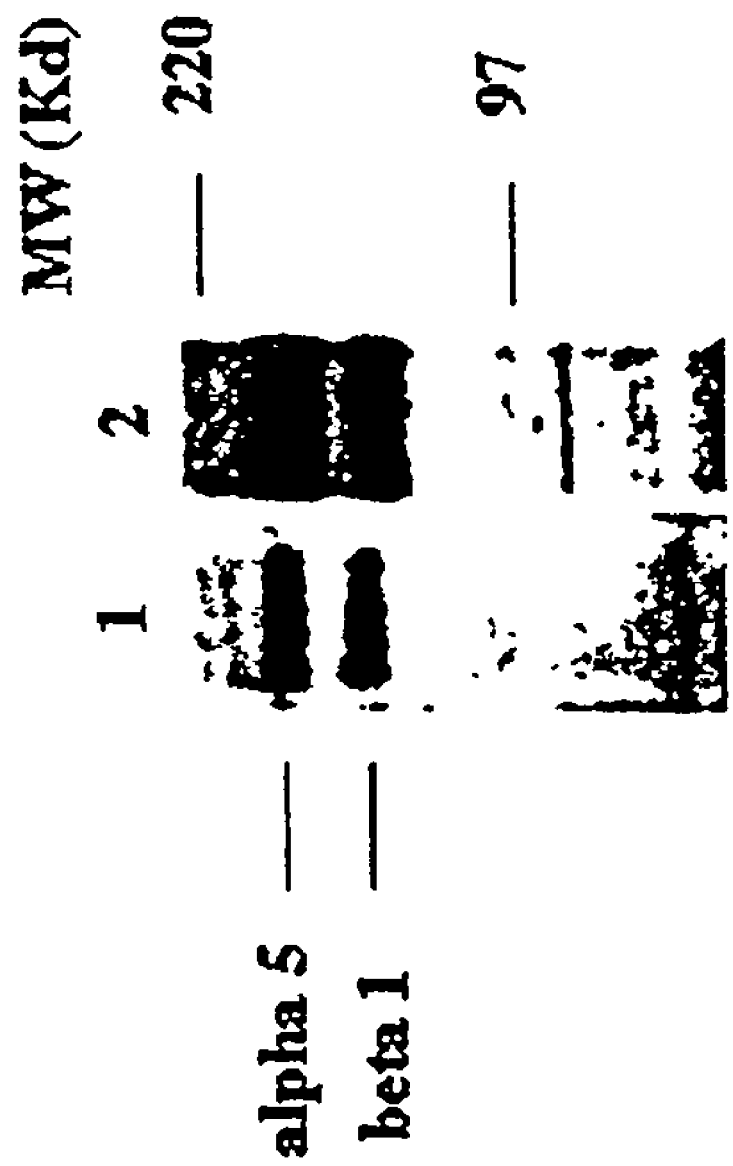
FIG. 1: Shows the results of the purification of the β1 integrin, α5β1, from placental lysates utilizing the 110 kD cell binding domain of fibronectin.

In accordance with the present invention, it has been discovered that protein-protein interactions involving certain sequences within the proteolytic enzyme MMP-9 and/or β1 integrin receptors contribute to angiogenesis and/or tumor growth by localizing the proteolytic activity to the cell surface. Thus, modifying such protein-protein interactions involving certain sequences found within the MMP-9 and/or β1 integrin receptors can inhibit angiogenesis and/or tumor growth.

The Interaction Between MMP-9 and β1 Integrins

In the physiological state, the synthesis of connective tissues is in dynamic equilibrium with the degradation of the extracellular matrix. That degradation is due, in part, to matrix metalloproteases ("MMPs"), a family of proteases (enzymes) involved in the degradation and remodeling of connective tissues. Members of this family of endopeptidase enzymes are secreted as proenzymes from various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes and cartilage. The MMPs share a number of properties, including zinc and calcium dependence, secretion as zymogens, and 40-50% amino acid sequence homology.

Excessive degradation of extracellular matrix by MMPs is implicated in the pathogenesis of many diseases of both chronic and acute nature. For example, numerous studies, as reviewed in Exp. Opin. Invest. Drugs, 5, 323-335, (1996), have established that expression and activation of MMPs are critical events in tumor growth, invasion and metastasis. In addition, MMP activity has been found to be required for angiogenesis, which is necessary for tumor growth as well as for other pathological conditions such as macular degeneration.

The members of this family of enzymes includes, but is not limited to, collagenases (MMP-1), gelatinases or collagenases of type IV (MMP-2, MMP-9), matrilysin (MMP-7, PUMP-1), and stromelysins (MMP-3).

Of particular interest here, the gelatinase MMP-9 is a 92-kD enzyme released by mononuclear phagocytes, neutrophils, corneal epithelial cells, tumor cells, cytotrophoblasts and keratinocytes.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (Cams) including the selectins, integrins, cadherins and immunoglobulins. Cams play an essential role in both normal and pathophysiological processes. Therefore, the targeting of specific and relevant Cams in certain disease conditions without interfering with normal cellular functions is essential for an effective and safe therapeutic agent that inhibits cell-cell and cell-matrix interactions.

Of the various Cams discussed above, the integrin superfamily is found in various combinations on nearly every mammalian cell type. (for reviews see: E. C. Butcher, Cell, 67, 1033 (1991); T. A. Springer, Cell, 76, 301 (1994); D. Cox et al., "The Pharmacology of the Integrins." Medicinal Research Rev. 14, 195 (1994) and V. W. Engleman et al., "Cell Adhesion Integrins as Pharmaceutical Targets." in Ann. Repts. in Medicinal Chemistry, Vol. 31, J. A. Bristol, Ed.; Acad. Press, NY, 1996, p. 191).

The integrins represent one of the best characterized superfamilies of adhesion receptors. Integrins are glycoprotein heterodimers which contain a non-covalently associated .alpha. (α) and .beta. (β) subunit. Integrin subunits are transmembrane proteins which contain an extracellular domain for interacting with an extracellular matrix or cellular component, a transmembrane domain spanning the cell membrane and a cytoplasmic domain for interacting with one or more cytoskeletal components.

There are fourteen known α subunits and eight known .beta. subunits which can pair to form at least twenty different integrin molecules. Several distinct integrin α chains are capable of pairing with one type of .beta. chain to form a .beta. chain subfamily.

Of particular interest here is the .beta..sub.1 (β1) subfamily, which includes seven members (also known as the VLA proteins: α1β1-α7β1). As the examples below show, angiogenesis and disease states can be inhibited using antagonists for modifying the protein-protein interactions involving certain amino acid sequences of the β1 integrins, α5β1 integrin being an example of such integrins. Throughout this specifications the terms β1 integrins and β1 containing integrins are used interchangeably.

Antagonists of the Invention

The examples provided herein establish that MMP-9 binds directly with the β1 integrin, α5β1 integrin. Thus, cells lacking the gene for making β1 integrins have a considerably reduced capacity for binding MMP-9. The examples also suggest that MMP-9 and α5β1 integrin may co-localize on the surface of a cell and blood vessels because they indicate that MMP-9 and α5β1 integrin are closely associated within both the human vascular compartment as well as on the tumor cells themselves.

Further, an analysis of the amino acid sequences of MMP-9 and α5β1 integrin leads to a polypeptide identified as FRIP-1 (SEQUENCE ID NO: 1) for mediating the interaction between these two proteins. FRIP-1 binds to MMP-9 but a control peptide AAAA (SEQUENCE ID NO: 3) binds with substantially reduced affinity to MMP-9. FRIP-1 was found to inhibit angiogenesis.

Moreover, as the examples show, FRIP-1 can be used to identify antagonists for modifying the protein-protein interactions involving certain amino acid sequences within MMP-9 and/or α5β1 integrin. Thus, Mab FM155 was identified by injecting mice with FRIP-1 conjugated to a carrier protein. Mab FM155 was found to have a high specificity for FRIP-1 but did not react with the control peptide AAAA: SEQUENCE ID NO: 3.

The examples illustrate that Mab FM155 can potently inhibit tumor growth in vivo. Thus, Mab FM155 modifies the protein-protein interactions involving certain amino acid sequences within MMP-9 and/or α5β1 integrin.

Antagonists of the invention may be any type of molecule, including, but not limited to, peptides, polypeptides, non-peptidic molecules, for example, organic molecules and oligonucleotides, proteins, enzymes, antibodies, monoclonal and polyclonal, etc.

Antagonists of the invention bind to FRIP-1 but bind to the control peptide AAAA with substantially reduced affinity. Apparent affinities can be determined by methods such as an enzyme linked immunosorbent assay (ELISA) or any other technique familiar to one of skill in the art. True affinities can be measured by techniques known to one of skill in the art.

Further, as would be known to one of ordinary skill in the art, other antagonists directed specifically to the epitope defined by Mab FM155 can have similar anti-angiogenic and anti-tumor activities. Such antagonists include additional function blocking Mabs, humanized Mabs, chimeric Mabs, toxin conjugated Mabs, polyclonal antibodies, small peptide antagonists directed to this epitope, as well as organic and non-peptidic mimetics of the epitope defined by FM155. In addition, the epitopes defined by the monoclonal antibody FM155 may themselves function as potent anti-angiogenic and/or anti-tumor compounds. Moreover, peptides containing epitopes recognized by an antagonist can be used themselves. Thus, the invention can take on several embodiments.

For example, one embodiment of the invention is an antagonist that specifically modifies protein-protein interactions, wherein the protein-protein interactions comprise interactions between at least one amino acid sequence within a first protein and at least one amino acid sequence within a second protein. The first protein of such an antagonist can be MMP-9 or it can be β1-containing integrin. Alternatively, the first protein can be MMP-9 and the second protein can be a β1-containing integrin. Further, in such a case, the protein-protein interactions may be such as to cause MMP-9 to bind to the β1-containing integrin.

Alternatively, when the first protein is a β1-containing integrin it can be α5β1 integrin or when the second protein is a β1-containing integrin it can be α5β1 integrin In one embodiment, the antagonist is such that the protein-protein interaction causes the co-localization of the first protein and the second protein on a cell surface or a blood vessel.

An antagonist of the invention is an antagonist that inhibits angiogenesis, tumor growth, or metastasis. In the general case, it can be an antagonist that inhibits a disease. Examples of such diseases are psoriasis, macular degeneration, a neurological disease, and restenosis in a tissue.

In another embodiment the antagonist of the invention is a monoclonal antibody. For example, it can be Mab FM155, it can be a monoclonal antibody having the binding specificity for at least one target of monoclonal antibody FM155, a humanized or chemically modified monoclonal antibody, or a fragment of a monoclonal antibody. Alternatively it could be a polyclonal antibody.

In a further embodiment, the antagonist of the invention is a polypeptide, a linear peptide or a cyclic peptide. Or it could be a non-peptidic compound. For example, the antagonist of the invention could be a small organic compound or an oligonucleotide.

In one embodiment, the antagonist of the invention is conjugated to cytotoxic or cytostatic agents.

In another embodiment, the invention is a polypeptide for inhibiting angiogenesis or tumor growth wherein the polypeptide specifically binds to MMP-9 with a binding capacity significantly greater than the binding capacity of SEQUENCE ID NO: 3 to MMP-9. For example, such a polypeptide is a protein.

In a preferred embodiment the polypeptide of the invention is SEQUENCE ID NO: 1. Alternatively, the polypeptide is such that the amino acid sequence of the polypeptide comprises SEQUENCE ID NO: 1.

In a further embodiment, the polypeptide of the invention is a monoclonal antibody. For example, the polypeptide could be the monoclonal antibody FM155.

In another embodiment, the invention is a polypeptide for inhibiting angiogenesis or tumor growth wherein the polypeptide specifically binds to a β1 containing integrin with a binding capacity significantly greater than the binding capacity of SEQUENCE ID NO: 3 to the β1 containing integrin. In this embodiment, the polypeptide is a protein, SEQUENCE ID NO: 1, a polypeptide the amino acid sequence of which comprises SEQUENCE ID NO: 1, or a monoclonal antibody, for example, FM 155.

In another embodiment, the invention is an antagonist that specifically binds with SEQUENCE ID NO: 1 but binds to SEQUENCE ID NO: 3 with substantially reduced affinity. Such an antagonist inhibits angiogenesis and tumor growth. In this embodiment, the antagonist is a polypeptide, for example, a protein, or it is a polypeptide the amino acid sequence of which comprises SEQUENCE ID NO: 1. The polypeptide may be a monoclonal antibody, for example, FM 155.

In another embodiment, the invention is an antagonist that disrupts the localization of MMP-9 on a cell surface or blood vessel. In this embodiment, the antagonist is such that it inhibits angiogenesis and tumor growth. Further, such an antagonist is a polypeptide, for example a protein, a polypeptide the amino acid sequence of which comprises SEQUENCE ID NO: 1, or a monoclonal antibody, for example, FM 155.

In another embodiment, the invention is a peptide comprising a sequence encoding an epitope recognized by an antagonist that specifically modifies protein-protein interactions, wherein the protein-protein interactions comprise interactions between at least one amino acid sequence within a first protein and at least one amino acid sequence within a second protein. In one version of this embodiment, the antagonist is a monoclonal antibody, for example, the Mab FM155. In another variation, the peptide consists of the amino acid sequence of SEQ ID NO: 1.

Antibody Antagonists

The present invention describes, in one embodiment, antagonists in the form of antibodies, which, in the general case, modify protein-protein interactions involving certain amino acid sequences within MMP-9 and/or β1 integrin. Such antibodies could include antibodies that bind to a peptide with a polypeptide sequence, SEQUENCE ID NO: 1: but do not bind to a control peptide sequence of SEQUENCE ID NO: 3. Such antibody antagonists also can inhibit angiogenesis. The invention also describes cell lines which produce the antibodies, methods for producing the cell lines, and methods for producing the monoclonal antibodies.

Antibodies of the invention can be monoclonal or polyclonal. In one embodiment, antibodies used are monoclonal. A monoclonal antibody of this invention comprises antibody molecules that immunoreact with MMP-9 and α5β1 integrin.

Preferred monoclonal antibodies which preferentially bind to FRIP-1 include monoclonal antibodies referred to as FM155.

Antibody antagonists of the invention can be generated according to a number of methods known to one of skill in the art. For example, an animal can be immunized with FRIP-1 or fragment thereof. Antibodies thus generated can be selected both for their ability to bind to FRIP-1 (SEQUENCE ID NO: 1) but not to bind to control SEQUENCE ID NO: 3.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules and those portions of an immunoglobulin molecule that contain the paratope, including those portions known in the art as Fab, Fab', F(ab')$_2$ and F(v), and also referred to as antibody fragments.

In another preferred embodiment, the invention contemplates a truncated immunoglobulin molecule comprising a Fab fragment derived from a monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods.

For example, Fab and F(ab')$_2$ portions (fragments) of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions also are well known and are produced from F(ab').sub.2 portions followed by reduction of the disulfide bonds linking the two heavy chain portions as with mercaptoethanol, and followed by alkylation of the resulting protein mercaptan with a reagent such as iodoacetamide. An antibody containing intact immunoglobulin molecules are preferred, and are utilized as illustrative herein.

The phrase "monoclonal antibody" in its various grammatical forms refers to a population of antibody molecules that contain only one species of antibody combining site capable of immunoreacting with a particular epitope. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, Nature 256:495-497 (1975), which description is incorporated by reference. Additional methods are described by Zola, Monoclonal Antibodies: A Manual of Techniques, CRC Press, Inc. (1987). The hybridoma supernatants so prepared can be screened for the presence of antibody molecules that immunoreact with MMP-9 and/or α5β1 integrin.

Briefly, to form the hybridoma from which the monoclonal antibody composition is produced, a myeloma or other self-perpetuating cell line is fused with lymphocytes obtained from the spleen of a mammal hyperimmunized with FRIP-1.

It is preferred that the myeloma cell line used to prepare a hybridoma be from the same species as the lymphocytes. Typically, a mouse of the strain 129 GlX.sup.+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to a selective growth medium, such as HAT (hypoxanthine aminopterin thymidine) medium. Hybridomas producing a monoclonal antibody of this invention are identified using the enzyme linked immunosorbent assay (ELISA) described in the Examples.

A monoclonal antibody of the present invention also can be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396, 1959) supplemented with 4.5 g/L glucose, 20 nM glutamine, and 20% fetal calf serum. An exemplary inbred mouse strain is the Balb/c.

Other methods of producing a monoclonal antibody, a hybridoma cell, or a hybridoma cell culture also are well known. See, for example, the method of isolating monoclonal antibodies from an immunological repertoire as described by Sastry et al. (1989) Proc. Natl. Acad. Sci. USA, 86:5728-5732; and Huse et al. (1989) Science, 246:1275-1281.

Also contemplated by this invention is the hybridoma cell, and cultures containing hybridoma cells that produce monoclonal antibodies of this invention. Particularly preferred is a hybridoma cell line that secretes monoclonal antibody FM155.

The invention contemplates, in one embodiment, a monoclonal antibody that has the immunoreaction characteristics of FM155.

One of skill in the art will know how to determine if a monoclonal antibody has an equivalent specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art. This does not suggest that antibodies with distinct CDR regions cannot bind to the same epitope.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Use of the term "having the binding specificity of" indicates that equivalent monoclonal antibodies compete for binding to a preselected target epitope.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention.

Thus, the invention contemplates, in one embodiment, a monoclonal antibody of this invention that is humanized by grafting to introduce components of the human immune system without substantially interfering with the ability of the antibody to bind antigen.

The antibody of the invention can also be a fully human antibody such as those generated, for example, by selection from an antibody phage display library displaying human single chain or double chain antibodies such as those described in de Haard, H. J. et al. (1999) J. Biol. Chem. 274:18218-30 and in Winter, G. et al. (1994) Annu. Rev. Immunol. 12:433-55.

Peptide/Polypeptide Antagonists

Antagonists of the invention also can be polypeptides or peptides. The term polypeptide refers to a sequence of 3 or more amino acids connected to one another by peptide bonds between the alpha-amino group and carboxy group of contiguous amino acid residues, and includes within its meaning the class of compounds known as proteins. The term peptide as used herein refers to a linear series of two or more connected to one to the other as in a polypeptide.

In one embodiment, the invention contemplates antagonists in the form of polypeptides. A polypeptide antagonist of the localization of MMP-9 to the cell surface can be any peptide or polypeptide capable of disrupting the localization of MMP-9 to the cell surface or, more generally, of modifying protein-protein interactions involving certain amino acid sequences within MMP-9 and/or β1 integrin.

The identification of preferred antagonist peptides having selectivity for MMP-9 or β1 integrins can readily be identified in a typical inhibition of binding assay, such as the ELISA assay described in the Examples.

Peptide and polypeptide antagonists can be generated by a number of techniques known to one of skill in the art. For example, a two hybrid system (e.g., Fields, S. (1989) Nature 340:245-6) can use a fragment of MM-9 as "bait" for selecting protein antagonists from a library that bind to the FRIP-1. The library of potential antagonists can be derived from a cDNA library, for example. In another embodiment, the potential antagonists can be variants of known MMP-9 binding proteins. Such proteins can be randomly mutagenized or subjected to gene shuffling, or other available techniques for generating sequence diversity.

Peptide and polypeptide antagonists of the invention also can be generated by techniques of molecular evolution. Libraries of proteins can be generated by mutagenesis, gene shuffling or other available techniques for generating molecular diversity. Protein pools representing numerous variants can be selected for their ability to bind to FRIP-1, for instance by passing such protein pools over a solid matrix to which a FRIP-1 has been attached. Elution with gradients of salt, for example, can provide purification of variants with affinity for the FRIP-1. A negative selection step also can be included whereby such pools are passed over a solid matrix to which the control peptide AAAA (SEQUENCE ID NO: 3) has been attached. The filtrate will contain those variants within the pool that have a reduced affinity for the AAAA.

Peptide and polypeptide antagonists of the invention also can be generated by phage display. A randomized peptide or protein can be expressed on the surface of a phagemid particle as a fusion with a phage coat protein. Techniques of monovalent phage display are widely available (see, e.g., Lowman H. B. et al. (1991) *Biochemistry* 30:10832-8.) Phage expressing randomized peptide or protein libraries can be panned with a solid matrix to which a AAAA molecule has been attached. Remaining phage do not bind AAAA, or bind AAAA with substantially reduced affinity. The phage are then panned against a solid matrix to which a FRIP-1 has been attached. Bound phages are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

In another embodiment, a polypeptide includes any analog, fragment or chemical derivative of a polypeptide whose amino acid residue sequence is shown herein so long as the polypeptide is an antagonist of FRIP-1 but not of the control peptide of SEQUENCE ID NO: 3. Therefore, a present polypeptide can be subject to various changes, substitutions, insertions, and deletions where such changes provide for certain advantages in its use. In this regard, a FRIP-1 antagonist polypeptide of this invention corresponds to, rather than is identical to, the sequence of a recited peptide where one or more changes are made and it retains the ability to function as an antagonist of the invention in one or more of the assays as defined herein.

Thus, a polypeptide can be in any of a variety of forms of peptide derivatives, that include amides, conjugates with proteins, cyclized peptides, polymerized peptides, analogs, fragments, chemically modified peptides, and like derivatives.

Other Antagonists

Antagonists of the invention also can be small organic molecules, such as those natural products, or those compounds synthesized by conventional organic synthesis or combinatorial organic synthesis. Compounds can be tested for their ability to modify protein-protein interactions involving certain amino acid sequences within MMP-9 and/or β1 integrin. Compounds also are selected for reduced affinity for the control peptide AAAA, SEQUENCE ID NO:3.

Antagonists of the invention also can be non-peptidic compounds. Suitable non-peptidic compounds include, for example, oligonucleotides. Oligonucleotides as used herein refers to any heteropolymeric material containing purine, pyrimidine and other aromatic bases. DNA and RNA oligonucleotides are suitable for use with the invention, as are oligonucleotides with sugar (e.g., 2' alkylated riboses) and backbone modifications (e.g., phosphorothioate oligonucleotides). Oligonucleotides may present commonly found purine and pyrimidine bases such as adenine, thymine, guanine, cytidine and uridine, as well as bases modified within the heterocyclic ring portion (e.g., 7-deazaguanine) or in exocyclic positions. Oligonucleotide also encompasses heteropolymers with distinct structures that also present aromatic bases, including polyamide nucleic acids and the like.

An oligonucleotide antagonist of the invention can be generated by a number of methods known to one of skill in the art. In one embodiment, a pool of oligonucleotides is generated containing a large number of sequences. Pools can be generated, for example, by solid phase synthesis using mixtures of monomers at an elongation step. The pool of oligonucleotides is sorted by passing a solution containing the pool over a solid matrix to which FRIP-1 or fragment thereof has been affixed. Sequences within the pool that bind to the MMP-9 are retained on the solid matrix. These sequences are eluted with a solution of different salt concentration or pH. Sequences selected are subjected to a second selection step. The selected pool is passed over a second solid matrix to which SEQUENCE ID NO: 3: has been affixed. The column retains those sequences that bind to the SEQUENCE ID NO: 3, thus enriching the pool for sequences specific for FRIP-1. The pool can be amplified and, if necessary, mutagenized and the process repeated until the pool shows the characteristics of an antagonist of the invention. Individual antagonists can be identified by sequencing members of the oligonucleotide pool, usually after cloning said sequences into a host organism such as *E. coli*.

Binding Assays for Identifying Antagonists

The invention also provides assay methods for identifying candidate antagonists for use according to the methods of the invention. In these assay methods candidate antagonists are evaluated for their ability to bind both FRIP-1 and the AAAA control peptide, and furthermore can be evaluated for their potency in inhibiting angiogenesis in a tissue.

ELISA

The first assay measures binding of antagonists to FRIP-1 and the AAAA control peptide in the solid phase by ELISA. The assay also can be used to identify compounds which exhibit specificity for FRIP-1 but not the AAAA control peptide. The specificity assay is conducted by running parallel ELISAs where a potential antagonist is screened concurrently in separate assay chambers for the ability to bind FRIP-1 and the AAAA control peptide.

Antagonists that disrupt the interaction between MMP-9 and α5β1 integrin can also be identified by their ability to compete for binding with an antagonist of the invention. For example, putative antagonists can be screened by monitoring their effect on the affinity of a known antagonist, such as FM155, in a binding assay, such as ELISA. Such antagonists likely have the same specificity as FM155, and recognize the same cryptic epitope. Putative antagonists selected by such a screening method can bind either to MMP-9 or α5β1 integrin or to the antagonist. Antagonists can be selected from the putative antagonists by conventional binding assays to determine those that bind to MMP-9 or α5β1 integrin epitope but not to the known antagonist.

Following are some embodiments of the invention that can be used to identify candidate antagonists.

In one embodiment, the invention is a method for screening for MMP-9 antagonists comprising: a) providing a putative antagonist; b) measuring said putative antagonist's first affinity for binding with MMP-9; c) measuring a second affinity of SEQUENCE ID NO: 3 for binding with MMP-9; and d) selecting said putative antagonist as an MMP-9 antagonist if said second affinity is substantially less than said first affinity. In one version of this embodiment, the putative antagonist is a non-peptidic compound, for example, a small organic compound or an oligonucleotide. In another version, the putative antagonist is a polypeptide, a linear peptide or a cyclic peptide. Alternatively, the putative antagonist is an antibody, which could be a monoclonal or polyclonal antibody.

In a preferred embodiment of this method, said first and said second affinities are measured by an enzyme linked immunosorbent assay.

In one particular embodiment, the second affinity is about 3 times less than the first affinity. Alternatively, the second affinity is about 5 times less than the first affinity. In a further embodiment of the invention, the second affinity is about 10 times less than the first affinity.

In one embodiment, the invention is a method for screening for β1 integrin antagonists comprising: a) providing a putative antagonist; b) measuring said putative antagonist's first affinity for binding with a β1 integrin; c) measuring a second affinity of SEQUENCE ID NO: 3 for binding with said β1 integrin; and d) selecting said putative antagonist as the β1 integrin antagonist if said second affinity is substantially less than said first affinity. In one version of this embodiment, the putative antagonist is a non-peptidic compound, for example, a small organic compound or an oligonucleotide. In another version, the putative antagonist is a polypeptide, a linear peptide or a cyclic peptide. Alternatively, the putative antagonist is an antibody, which could be a monoclonal or polyclonal antibody.

In a preferred embodiment of this method, said first and said second affinities are measured by an enzyme linked immunosorbent assay.

In one particular embodiment, the second affinity is about 3 times less than the first affinity. Alternatively, the second affinity is about 5 times less than the first affinity. In a further embodiment of the invention, the second affinity is about 10 times less than the first affinity.

Angiogenesis Assays

Antagonists of the invention also can be assayed for their ability to modulate angiogenesis in a tissue. Any suitable assay known to one of skill in the art can be used to monitor such effects. Several such techniques are described herein.

For example, one assay measures angiogenesis in the chick chorioallantoic membrane (CAM) and is referred to as the CAM assay. The CAM assay has been described in detail by others, and further has been used to measure both angiogenesis and neovascularization of tumor tissues. See Ausprunk et al., *Am. J. Pathol.*, 79:597-618 (1975) and Ossonski et al., *Cancer Res.*, 40:2300-2309 (1980).

The CAM assay is a well recognized assay model for in vivo angiogenesis because neovascularization of whole tissue is occurring, and actual chick embryo blood vessels are growing into the CAM or into the tissue grown on the CAM.

As demonstrated herein, the CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

A second assay measures angiogenesis is the in vivo rabbit eye model and is referred to as the rabbit eye assay. The rabbit eye assay has been described in detail by others, and further has been used to measure both angiogenesis and neovascularization in the presence of angiogenic inhibitors such as thalidomide. See D'Amato et al. (1994) *Proc. Natl. Acad. Sci.* 91:4082-4085.

The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

A fourth assay measures angiogenesis in the chimeric mouse:human mouse model and is referred to as the chimeric mouse assay. The assay has been described in detail by others, and further has been described herein to measure angiogenesis, neovascularization, and regression of tumor tissues. See Yan, et al. (1993) *J. Clin. Invest.* 91:986-996.

The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity.

Methods for Inhibition of Angiogenesis

The invention provides for a method for the inhibition of angiogenesis in a tissue, and thereby inhibiting events in the tissue which depend upon angiogenesis. Generally, the method comprises administering to the tissue a composition comprising an angiogenesis-inhibiting amount of an antagonist that modifies protein-protein interactions involving certain amino acid sequences within MMP-9 and/or β1 integrins.

As described earlier, angiogenesis includes a variety of processes involving neovascularization of a tissue including "sprouting", vasculogenesis, or vessel enlargement, all of which angiogenesis processes involve disruption of extracellular matrix collagen in blood vessels. With the exception of traumatic wound healing, corpus leuteum formation and embryogenesis, it is believed that the majority of angiogenesis processes are associated with disease processes and therefore the use of the present therapeutic methods are selective for the disease.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma.

Thus, methods which inhibit angiogenesis in a diseased tissue ameliorate symptoms of the disease and, depending upon the disease, can contribute to cure of the disease. In one embodiment, the invention contemplates inhibition of angiogenesis, per se, in a tissue.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli. Tissue, as used herein, also encompasses all bodily fluids, secretions and the like, such as serum, blood, cerebrospinal fluid, plasma, urine, synovial fluid, vitreous humor.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate that the invention is effective with respect to all mammals, which are intended to be included in the term "patient". In this context, a mammal is understood to include any mammalian species in which treatment of diseases associated with angiogenesis is desirable, particularly agricultural and domestic mammalian species. Such a patient can be, for example, a pig, a cow, a horse, a goat, a sheep, a mule, a donkey, a dog, a cat, a rabbit, a mouse and a rat.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's Sarcoma and the like tissues. Exemplary tumor tissue angiogenesis, and inhibition thereof, is described in the Examples.

Inhibition of tumor tissue angiogenesis is a particularly preferred embodiment because of the important role neovascularization plays in tumor growth. In the absence of neovascularization of tumor tissue, the tumor tissue does not obtain the required nutrients, slows in growth, ceases additional growth, regresses and ultimately becomes necrotic resulting in killing of the tumor.

Stated in other words, the present invention provides for a method of inhibiting tumor neovascularization by inhibiting tumor angiogenesis. Similarly, the invention provides a method of inhibiting tumor growth by practicing the angiogenesis-inhibiting methods.

By their ability to inhibit neovascularization, the methods of the invention also are effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with other therapies such as conventional chemotherapy directed against solid tumors and for control of establishment of metastases. The administration of angiogenesis inhibitor is typically conducted during or after chemotherapy, although it is preferable to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

Insofar as the present methods apply to inhibition of tumor neovascularization, the methods also can apply to regression of established tumors.

Restenosis is a process of smooth muscle cell (SMC) migration and proliferation at the site of percutaneous transluminal coronary angioplasty which hampers the success of angioplasty. The migration and proliferation of SMCs associated with blood vessels during restenosis is related to the process of angiogenesis which is inhibited by the present methods. Therefore, the invention also contemplates inhibition of restenosis by inhibiting angiogenic related processes according to the present methods in a patient following angioplasty procedures. For inhibition of restenosis, the antagonist of the invention is typically administered after the angioplasty procedure for from about 2 to about 28 days, and more typically for about the first 14 days following the procedure.

The present method for inhibiting angiogenesis in a tissue, and therefore for also practicing the methods for treatment of angiogenesis-related diseases, comprises contacting a tissue in which angiogenesis is occurring, or is at risk for occurring, with a therapeutic composition comprising a therapeutically effective amount of an antagonist that modifies protein-protein interactions involving certain amino acid sequences within MMP-9 and/or β1 integrins. Thus, the method comprises administering to a patient a therapeutically effective amount of a physiologically tolerable composition containing an antagonist of the invention, which antagonist modifies protein-protein interactions involving certain amino acid sequences within MMP-9 and/or β1 integrins. Therapeutic compositions and therapeutically effective amounts of antagonists of the invention are described infra in the section entitled "Therapeutic Compositions."

The dosage ranges for the administration of the antagonist depend upon the form of the antagonist, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage also can be adjusted by the individual physician in the event of any complication.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, antagonists including monoclonal antibodies, polypeptides, and derivatives thereof can be administered intravenously, intraperitoneally, intramuscularly, subcutaneously, intracavity, transdermally, topically, intraocularly, orally, intranasally and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

In one preferred embodiment as shown in the Examples, the antagonist is administered in a single dosage intravenously.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As specific examples of methods for inhibiting angiogenesis or disease states, the following embodiments of the invention are offered.

In one embodiment, the invention is a method of inhibiting angiogenesis in a tissue comprising administering an antagonist that specifically modifies protein-protein interactions, wherein the protein-protein interactions comprise interactions between at least one amino acid sequence within a first protein and at least one amino acid sequence within a second protein. In this method, said antagonist is administered intravenously, transdermally, intrasynovially, intramuscularly, intratumorally, intraocularly, intranasally, intrathecally, topically or orally. Further, the antagonist may be administered in conjunction with chemotherapy or in conjunction with radiation. This method is used when the tissue is inflamed and angiogenesis is occurring, when the tissue is present in a mammal, or when the tissue is arthritic, ocular, retinal or a hemangioma.

In another method of treatment according to the invention, tumor growth or metastasis in a tissue is inhibited in a method comprising administering an antagonist that specifically modifies protein-protein interactions, wherein the protein-protein interactions comprise interactions between at least one amino acid sequence within a first protein and at least one amino acid sequence within a second protein. In such a method, said antagonist is administered intravenously, transdermally, intrasynovially, intramuscularly, intratumorally, intraocularly, intranasally, topically or orally. Further, the antagonist may be administered in conjunction with chemotherapy or in conjunction with radiation. This method would be applicable when the tumor or metastasis is a melanoma, carcinoma, sarcoma, fibrosarcoma, glioma or In another embodiment, the invention is a method of inhibiting psoriasis, macular degeneration, or restenosis in a tissue by administering an antagonist that specifically modifies protein-protein interactions, wherein the protein-protein interactions comprise interactions between at least one amino acid sequence within a first protein and at least one amino acid sequence within a second protein. In this method, said antagonist is administered intravenously, transdermally, intrasynovially, intramuscularly, intratumorally, intraocularly, intranasally, intrathecally, topically or orally. Further, the antagonist is administered in conjunction with chemotherapy or in conjunction with astrocytoma.

Disease Treatment

The present invention relates generally to the discovery that modifying protein-protein interactions involving certain amino acid sequences within MMP-9 and/or β1 integrins inhibits disease states and angiogenesis. This discovery is important because of the role that angiogenesis plays in a variety of disease processes.

Where the growth of new blood vessels is the cause of, or contributes to, the pathology associated with a disease, inhibition of angiogenesis will reduce the deleterious effects of the disease. Examples include psoriasis, rheumatoid arthritis, diabetic retinopathy, inflammatory diseases, restenosis, macular degeneration and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, only new vessel growth is inhibited by antagonists that disrupt the localization of MMP-9, and therefore the therapeutic methods do not adversely effect mature vessels. Also, because certain of the the antagonists of the invention affect only the localization of MMP-9, and do not directly block the proteolytic activity of MMP-9 or the adhesive functions of the β1 integrins, it is likely that these compounds will have fewer side effects because the proteolytic activity of MMP-9 or the adhesive functions of the β1 integrins may have normal physiological functions.

Moreover, the antagonists of the invention are highly potent suggesting that they may have therapeutic benefits at low concentrations.

Prior to the discoveries of the present invention, it was not known that angiogenesis, and any of the processes dependent on angiogenesis, could be inhibited in vivo by the use of reagents that antagonize the interaction between MMP-9 and the β1 integrins.

Therapeutic Compositions

The present invention contemplates therapeutic compositions useful for practicing the therapeutic methods described herein. Therapeutic compositions of the present invention contain a physiologically tolerable carrier together with a therapeutically effective amount of an antagonist as described herein, dissolved or dispersed therein as an active ingredient. In a preferred embodiment, the therapeutic antagonist composition is not immunogenic or has reduced immunogenicity when administered to a mammal or human patient for therapeutic purposes.

A therapeutically effective amount is an amount of an antagonist of the invention sufficient to produce a measurable inhibition of angiogenesis in the tissue being treated, i.e., an angiogenesis-inhibiting amount. Inhibition of angiogenesis can be measured in situ by immunohistochemistry, as described herein, or by other methods known to one skilled in the art.

Potency of an antagonist of the invention can be measured by a variety of means including inhibition of angiogenesis in the CAM assay, in the in vivo rabbit eye assay, in the in vivo chimeric mouse:human assay and the assays.

A therapeutically effective amount of an antagonist of this invention in the form of a monoclonal antibody is typically an amount such that when administered in a physiologically tolerable composition is sufficient to achieve a plasma concentration of from about 0.01 microgram (ug) per milliliter (mL) to about 100 ug/mL, preferably from about 1 ug/mL to about 5 ug/mL, and usually about 5 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Where the antagonist is in the form of a fragment of a monoclonal antibody, the amount can readily be adjusted based on the mass of the fragment relative to the mass of the whole antibody. A preferred plasma concentration in molarity is from about 2 micromolar (uM) to about 5 millimolar (mM) and preferably about 100 uM to 1 mM antibody antagonist.

A therapeutically effective amount of an antagonist of this invention in the form of a polypeptide, or small molecule, is typically an amount of polypeptide such that when administered in a physiologically tolerable composition is sufficient to achieve a plasma concentration of from about 0.1 microgram (ug) per milliliter (mL) to about 200 ug/mL, preferably from about 1 ug/mL to about 150 ug/mL. Based on a polypeptide having a mass of about 500 grams per mole, the preferred plasma concentration in molarity is from about 2 micromolar (uM) to about 5 millimolar (mM) and preferably about 100 uM to 1 mM polypeptide antagonist. Stated differently, the dosage per body weight can vary from about 0.1 mg/kg to about 300 mg/kg, and preferably from about 0.2 mg/kg to about 200 mg/kg, in one or more dose administrations daily, for one or several days.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred are the salts of TFA and HCl.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting amount of an antagonist of the present invention, typically formulated to contain an amount of at least 0.01 weight percent of antagonist per weight of total therapeutic composition. A weight percent is a ratio by weight of inhibitor to total composition. Thus, for example, 0.01 weight percent is 0.01 grams of inhibitor per 100 grams of total composition.

An antibody can be conjugated with cytotoxins, cytotoxic agents, for delivery to a to tumor or other tissue undergoing angiogenesis. Such conjugates can be made with a cytolysin or an exotoxin, for example ricin A, diphtheria toxin A, or *Pseudomonas* exotoxin and fragments thereof. The cytotoxic agent can also be radioactively labeled with an isotope so as to locally deliver a toxic dose of radioactivity to an angiogenic tissue.

Antagonists of the invention can also be used to deliver an enzyme to a target wherein the enzyme is capable of converting a prodrug into an active form of the drug for use in, for example, antibody-directed enzyme activated prodrug therapy (ADEPT) (see, e.g., Syrigos, K. N. (1999) *Anticancer Res.* 19:605-13). Briefly, an antagonist of the invention is conjugated with an enzyme, such as a lactamase, protease or esterase, that can convert a non-toxic or inactive prodrug into a toxic or active drug. Because the antagonist of the invention localizes to sites of angiogenesis, and particularly to sites of tumors or metastases, toxic drugs can be directed to such sites Detection Methods Antagonists of the invention also are suitable for detection of angiogenesis in tissues. For example, where the antagonist is an antibody, the antagonist can be used in immunohistochemical techniques to stain tissues ex vivo. Immunological techniques such as immunostaining and ELISA are described in, for example, *Receptor Binding Techniques Methods in Molecular Biology*. 106. ed. M. Keen. Humana Press, 1999; Brooks et al. (1998) *Cell* 92:391-400; Brooks et al. (1996) *Cell* 85:683-693; and Brooks et al. (1993) *J. Cell. Biol.* 122:1351-1359.

The antagonist of the invention, once bound to the target tissue can be detected either directly or indirectly. Direct detection can be performed on antagonists that comprise a detectable label such as a fluorochrome, a radioactive tag, paramagnetic heavy metal or diagnostic dye.

Alternatively, detection can occur through a secondary interaction. For example, a detectably labeled antibody that recognizes the antagonist can be used to visualize the location of the antagonist. For example, if the antagonist is a monoclonal antibody of mouse origin, a goat anti-mouse antibody that is suitably labeled can be used. One of skill in the art can determine suitable secondary antibodies for use with various antagonists.

For in vivo detection, it is preferable to use a detectably labeled antagonist. The labeled antagonist is administered to a patient intravenously, intramuscularly, etc. Labels suitable for detection within a patient are particularly preferred. For example, paramagnetically labeled antagonists can be detected by magnetic resonance imaging. Radioactively tagged antagonists also can be detected.

Examples of specific embodiments of the invention suitable for detection are as follows.

In one embodiment, the invention is a method of detecting angiogenesis in a tissue by contacting an antagonist that specifically modifies protein-protein interactions, wherein the protein-protein interactions comprise interactions between at least one amino acid sequence within a first protein and at least one amino acid sequence within a second protein with said tissue. In this method, for example, said tissue is ex vivo or said tissue is in vivo and said antagonist is administered intravenously, transdermally, intrasynovially, intramuscularly, intratumorally, intraocularly, intranasally, intrathecally, topically or orally. Alternatively, in this method said antagonist is conjugated to a fluorochrome, radioactive tag, paramagnetic heavy metal, diagnostic dye or enzyme.

All references cited herein are incorporated by reference in their entirety.

EXAMPLES

Example 1

Purification of α5β1

α5β1 was purified from placental lysates utilizing the 110 kD cell binding domain of fibronectin. Eluted fractions were concentrated and separated by 10% SDS PAGE followed by silver staining. A 90 kD protein co-purifies with integrin α5β1 with a molecular weight same as MMP-9 as shown in FIG. 1. In the figure, Lane 1 corresponds to commercially prepared human α5β1 (1 μg) and Lane 2 to α5β1 (50 μl) purified from human placental tissue. Note minor 90 kD contaminate (arrow).

Based on our previous finding of a direct interaction between MMP-2 and αuβ3, we examined whether this 90 kD protein may be another example of MMP binding to an integrin.

Example 2

Zymographic Analysis of α5β1

Figure 2:
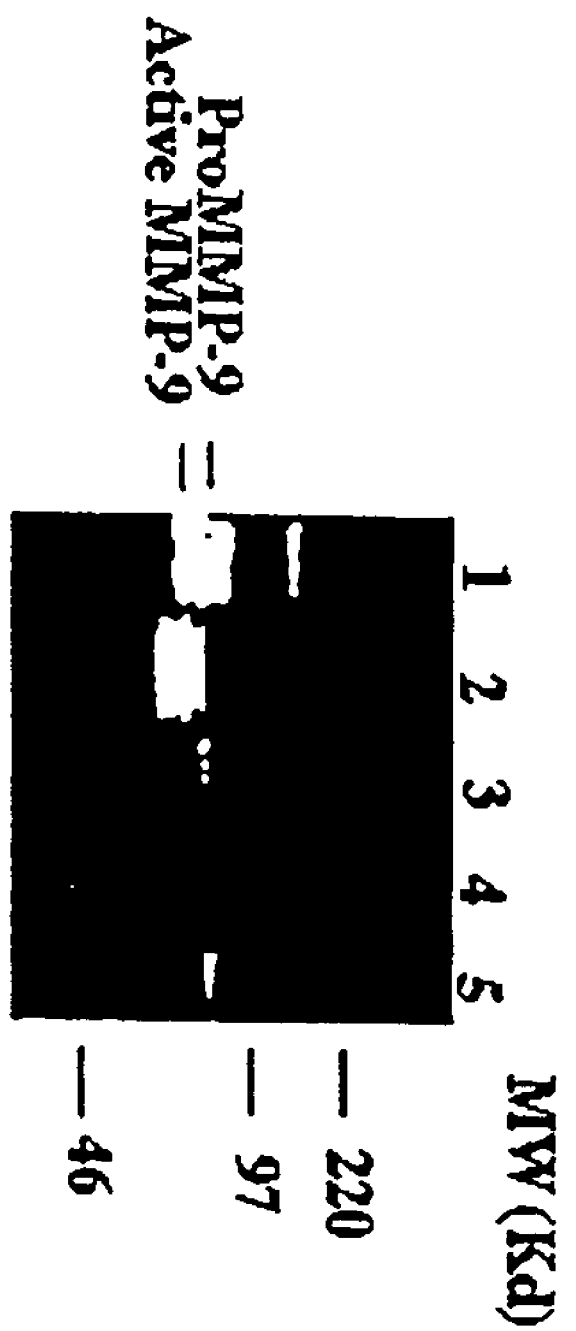
FIG. 2: Show the results of zymographic analysis of the β1 integrin, α5β1, when purified α5β1 and αvβ3 are separated on 10% SDS PAGE gels co-polymerized with gelatin.

Purified α5β1 and αvβ3 were separated on 10% SDS PAGE gels co-polymerized with gelatin. SDS was removed from the gels by washing in Triton X-100 and the gels were incubated in collagenase buffer. Gelatinolytic bands were visualized by staining with coomassie blue. The purified α5β1 preparation contains gelatinolytic activity (90 kD) that migrates at the same molecular weight as MMP-9 as shown in FIG. 2. In the figure, Lane 1 corresponds to Pro MMP-9 (1 μg), Lane 2 to APMA activated MMP-9 (1 μg), Lane 3 to prep-1 purified α5β1 from placental tissue (1 μg); Lane 4 to purified αvβ3 from placental tissue (1 μg) and Lane 5 to prep-2 purified α5β1 from placental tissue (1 μg).

These data suggest that the contaminating 90 kD protein that co-purified with a α5β1 may be MMP-9. Moreover, these studies suggest that MMP-9 may bind directly to integrin α5β1.

Example 3

Western Blot Analysis of Purified Integrins α5β1

Figure 3:
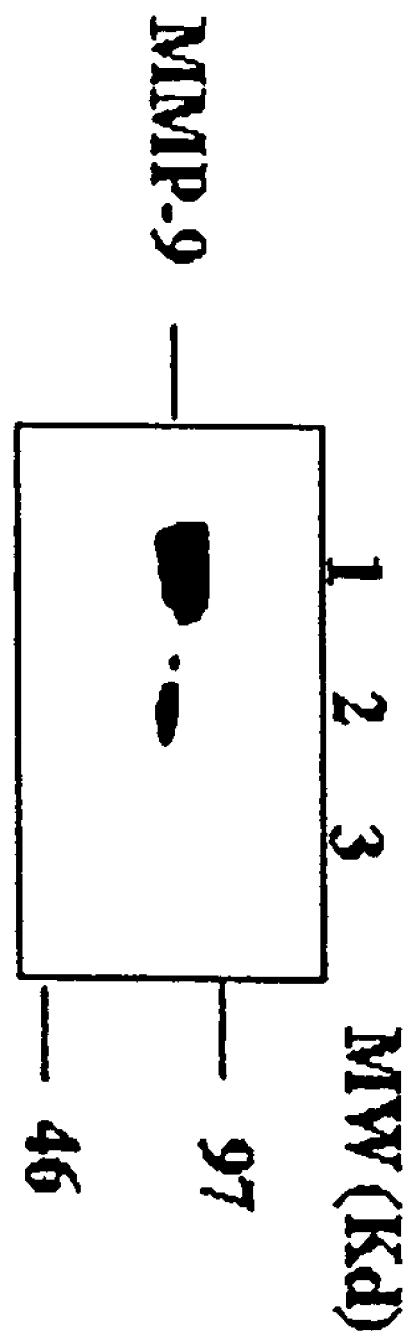
FIG. 3: Shows the results of Western Blot Analysis of the β1 integrin, α5β1, when purified integrins α5β1 and αvβ3 (1 μg) are separated.

Purified integrins α5β1 and αvβ3 (1 μg) were separated by 10% SDS PAGE and transferred to nitrocellulose and blotted with anti-MMP-9 Mab. Western blot analysis of the purified α5β1, shown in FIG. 3, with a monoclonal antibody directed to MMP-9 confirms the existence of MMP-9 within the preparation of α5β1. In FIG. 3, Lane 1 corresponds to Recombinant MMP-9 (1 μg), Lane 2 to purified α5β1 from placental tissue (1 μg) and Lane 3 to purified αvβ3 from placental tissue (1 μg).

Example 4

Figure 4:
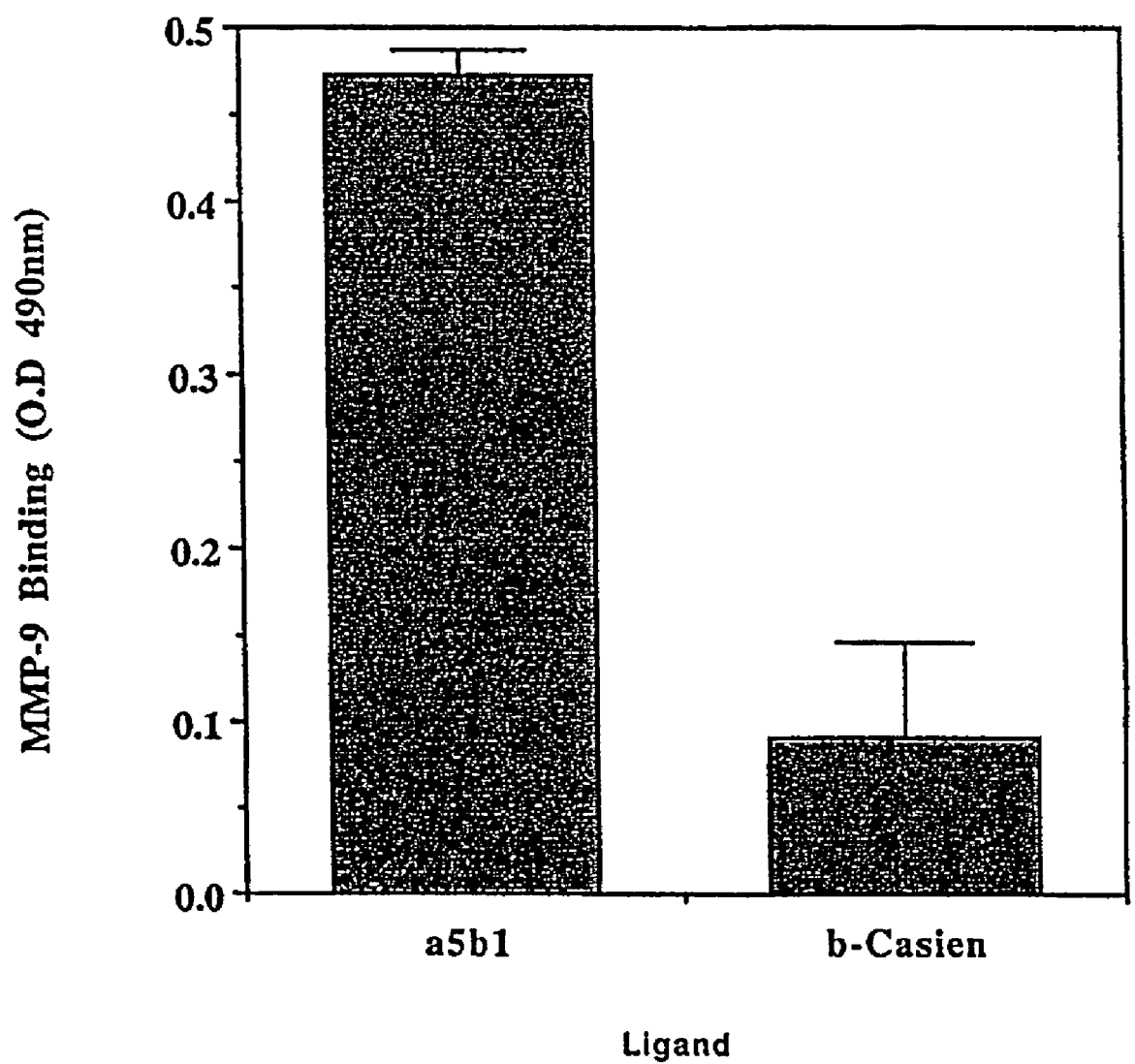
FIG. 4: Shows the results of binding assay for recombinant MMP-9 binding to the β1 integrin, α5β1, or control protein β-casein.

Recombinant MMP-9 Binds to α5β1

α5β1 or control protein β-casein was immobilized on microtiter wells (10 μg/ml). Recombinant human MMP-9 (2 μg/ml) was allowed to bind to control coated wells for one hour. MMP-9 binding was detected with anti-MMP-9 Mab. As can be seen from FIG. 4, purified MMP-9 binds directly to integrin α5β1. Data Bars represent the mean optical density ±standard deviations from triplicate wells.

Example 5

Reduced MMP-9 Binding to the Surface of α5β1 Negative Cells

Figure 5:
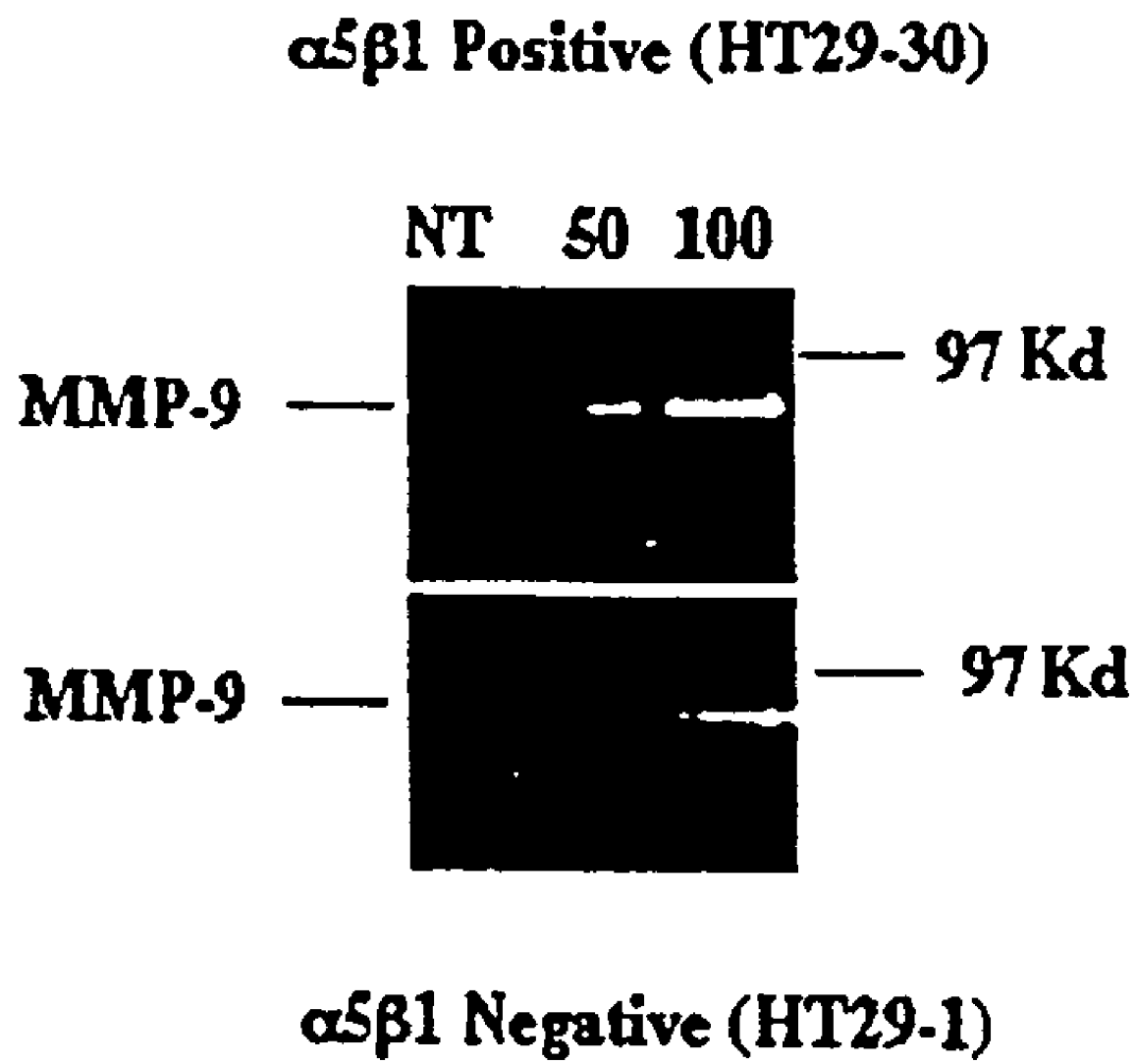
FIG. 5: Shows the results of experiments in which recombinant MMP-9 is incubated with α5β1 positive and negative cells.

To evaluate whether α5β1 may be involved in facilitating binding of MMP-9 to the cell surface, binding assays were performed. Human HT29 cells that express little if any endogenous MMP-9 were incubated with recombinant MMP-9 (0 to 100 ng/ml). Non-bound enzyme was removed and total cell lysates were prepared. Cell lysates (100 μg per lane) were separated on a 10% SDS PAGE gel co-polymerized with gelatin and gelatinolytic bands were visualized by staining with coomassie blue. The results shown in FIG. 5 suggest that tumor cells lacking α5β1 have a significantly reduced capacity to bind MMP-9, providing further evidence that α5β1 may play an important role in localizing proteolytic activity to the cell surface. In the figure, Top corresponds to α5β1 expressing HT29-30, Bottom to α5β1 negative HT29-1, NT to no treatment, 50 to Cells incubated with 50 ng/ml of MMP-9 and 100 to Cells incubated with 100 ng/ml of MMP-9.

Example 6

Co-Localization of MMP-9 and α5β1 in Human Melanoma Tumor Blood Vessels

Figure 6A:
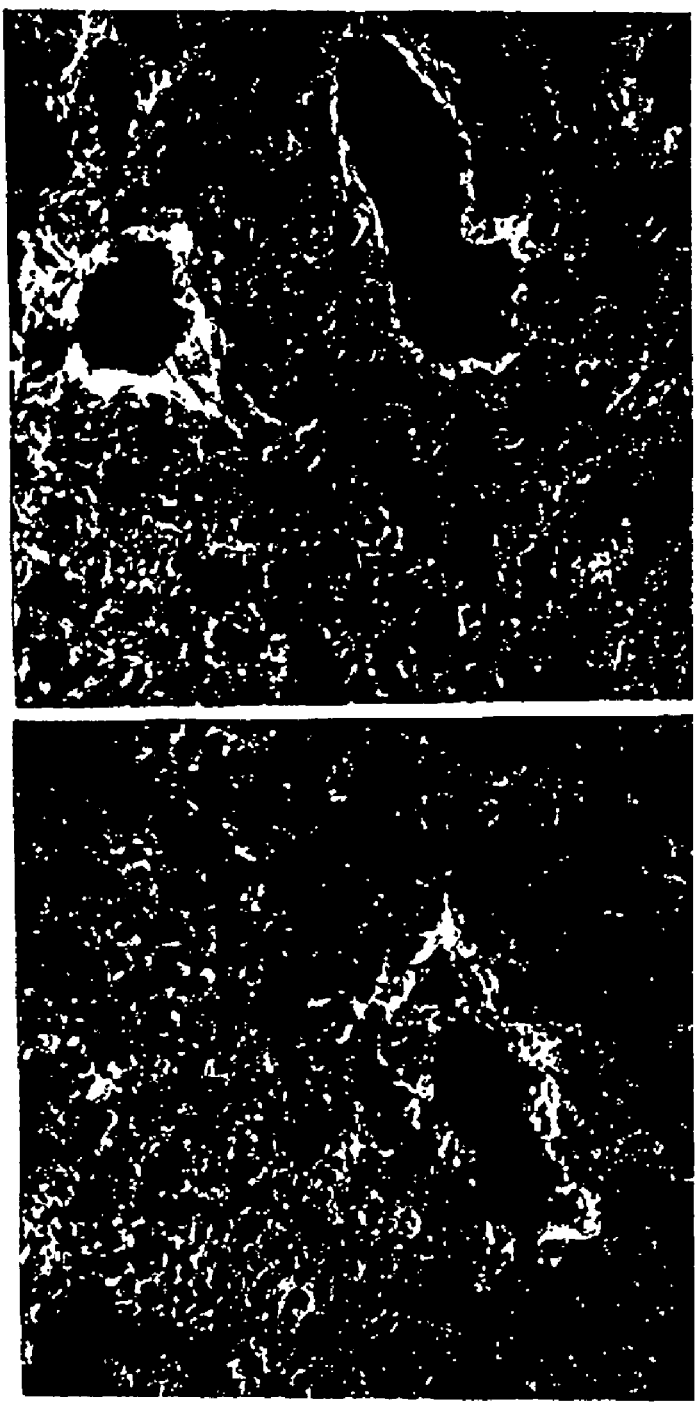
FIG. 6A/6B: Show the results of experiments to determine the co-localization of MMP-9 and, the β1 integrin, α5β1, in human melanoma tumor blood vessels.
Figure 6B:
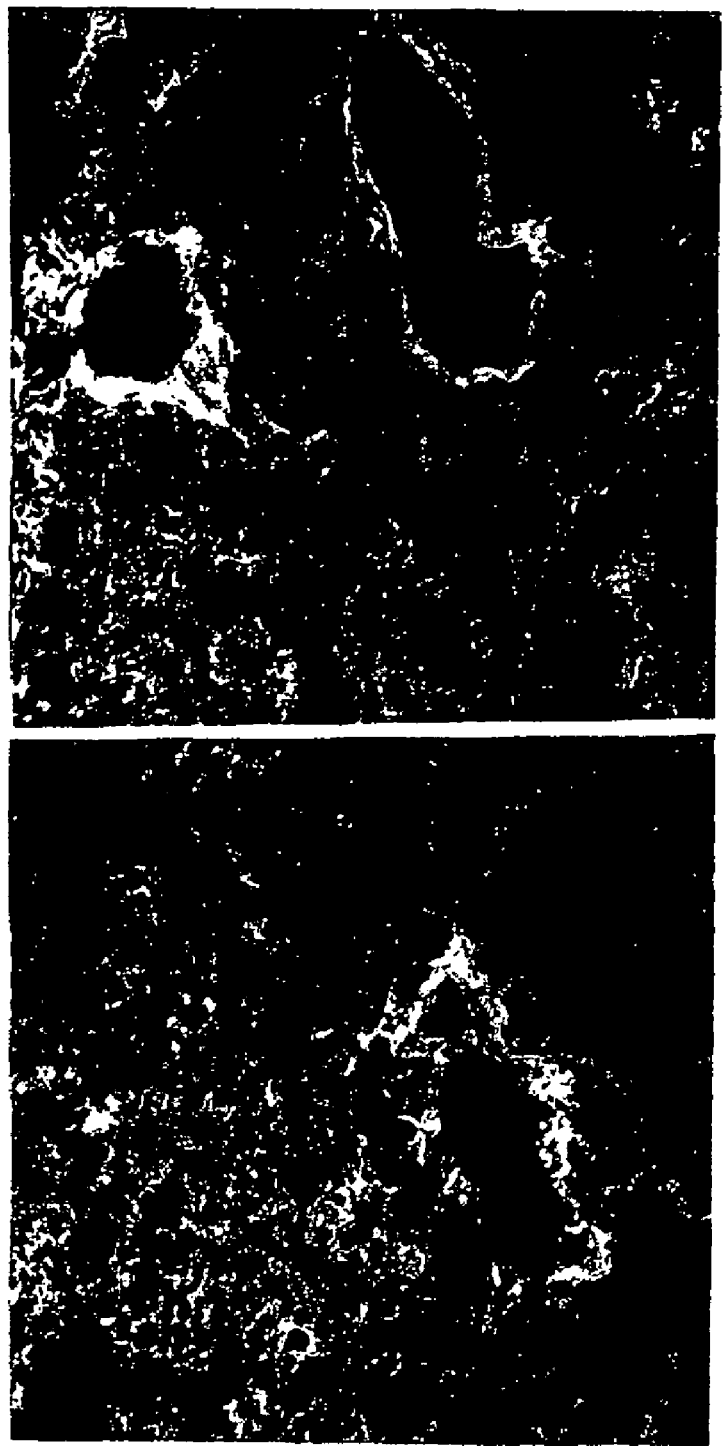

Human biopsies from melanoma patients were snap frozen and tissue sections were co-stained with a polyclonal antibody directed to MMP-9 and a monoclonal antibody directed to β1, followed by incubation with both rhodamine conjugated goat-anti-mouse and FITC conjugated goat-anti-rabbit IgGs. Photomicrographs were taken at 200×. In the photomicrograph, which is FIG. 6B, red indicated β1 integrin expression, green indicated MMP-9 expression, yellow indicated co-localization of MMP-9 and β1. In FIG. 6A, which is a black and white reproduction of the photomicrograph, the white regions represent yellow, and the black regions represent red, green, or the tumor cells. FIG. 6A shows that MMP-9 and β1 integrins co-localize on the tumor cell surface and blood vessels within human melanoma tumor biopsies.

These findings suggest that MMP-9 and β1 integrins are closely associated within both the human vascular compartment as well as on the tumor cells themselves.

Example 7

Generation of Synthetic Peptides that Bind to MMP-9

Analysis of the amino acid sequences of both MMP-9 and α5β1 suggested sequences that may mediate the interaction between these two proteins. For example, synthetic peptides were generated and analyzed for binding activity to MMP-9. The binding ability of the peptides was analyzed by solid phase binding assays.

Figure 7:
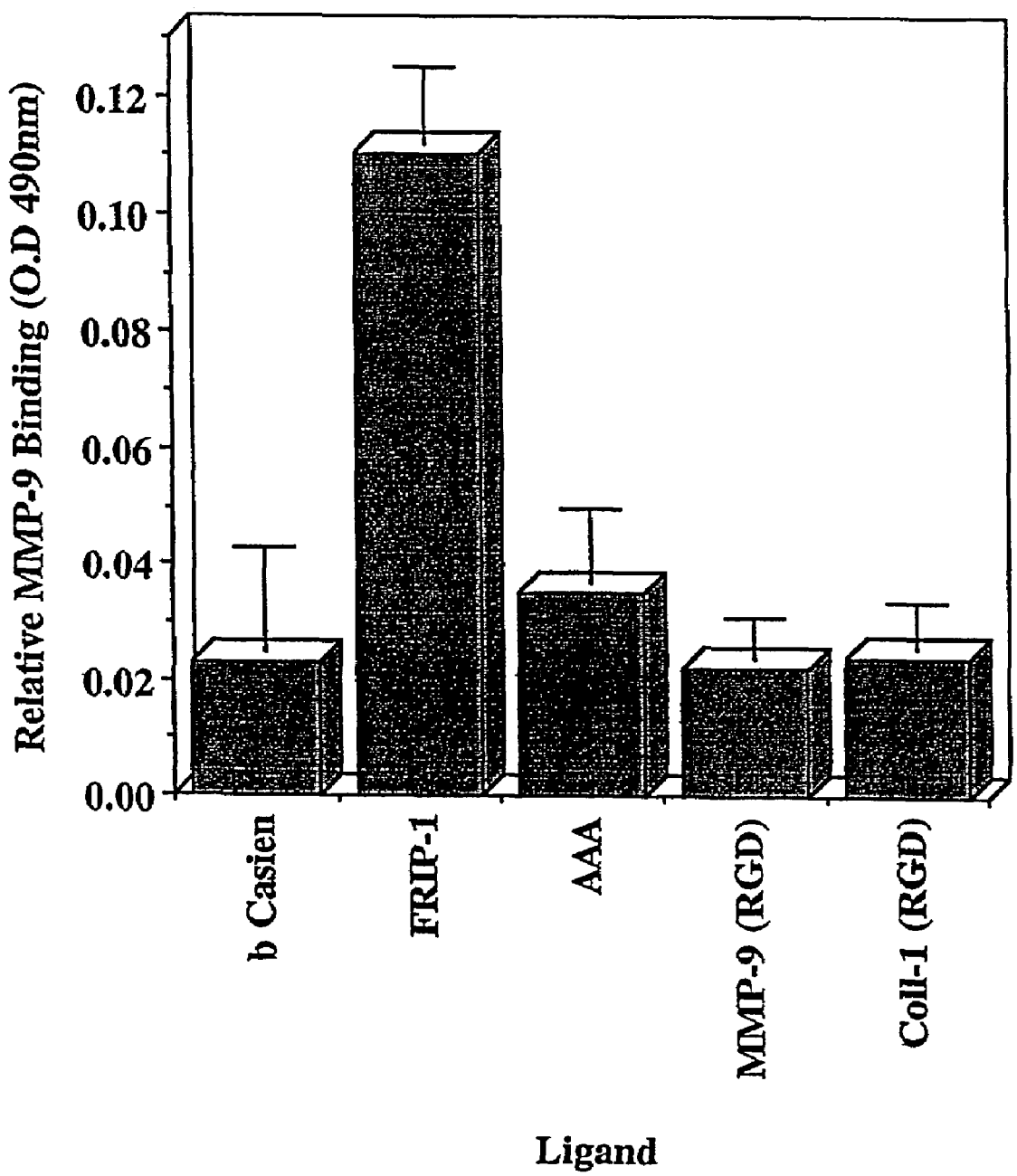
FIG. 7: Shows the results of experiments to identify synthetic peptides that bind to MMP-9. FRIP-1 is SEQUENCE ID NO:1 and AAA is the AAA peptide, which is SEQUENCE ID NO:2.

Among the sequences analyzed, peptides were found that showed binding specificity for MMP-9 or the β1 integrins. Thus, as shown in FIG. 7, the peptide termed FRIP-1 was shown to specifically bind to MMP-9 in solid phase binding assays. AAA peptide which was identical to FRIP-1 except that 3 key amino acids were changed showed little in any binding ability. These findings suggest that the synthetic peptide FRIP-1 likely represents key amino acids involved in mediating MMP-9/α5β1 interactions.

FRIP-1 synthetic peptide has the sequence: SEQ ID NO: 1: CysArgLeuArgSerGlyGluProGlnCys The FRIP1 (SEQ ID NO: 1) amino acid sequence was derived from a region within the C-terminal hemopexin-like domain of human enzyme MMP-9.

The AAA control peptide has the following sequence: SEQ ID NO: 2: CysArgAlaAlaAlaGlyGluProGlnCys Binding controls were also performed with a AAAA control peptide with the following sequence: SEQ ID NO: 3: CysArgAlaAlaAlaAlaGluProGlnCys.

Example 8

FRIP-1 Peptide Inhibits Angiogenesis in the Chick Embryo

Figure 8A:
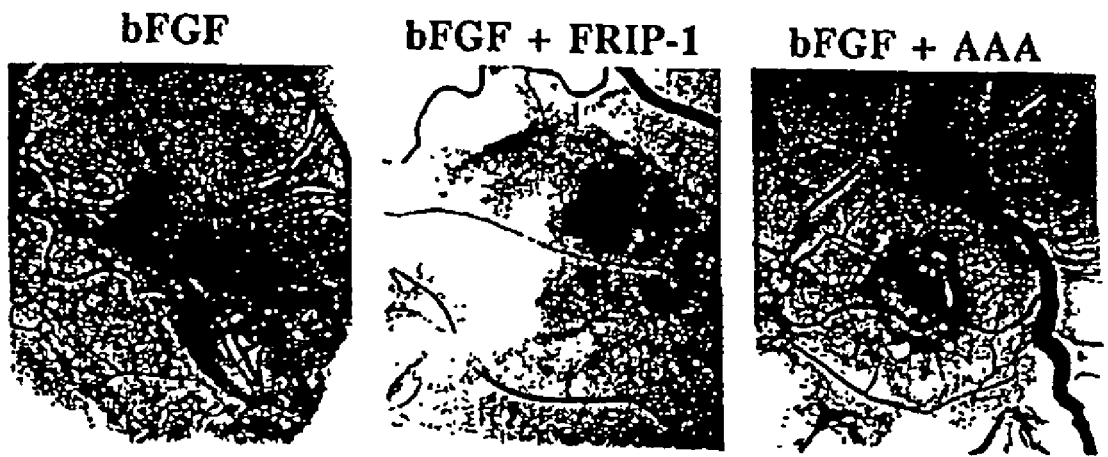
FIG. 8A/8B: Show the results of experiments in which the FRIP-1 peptide was injected into chick embryos in which angiogenesis had been induced.
Figure 8B:
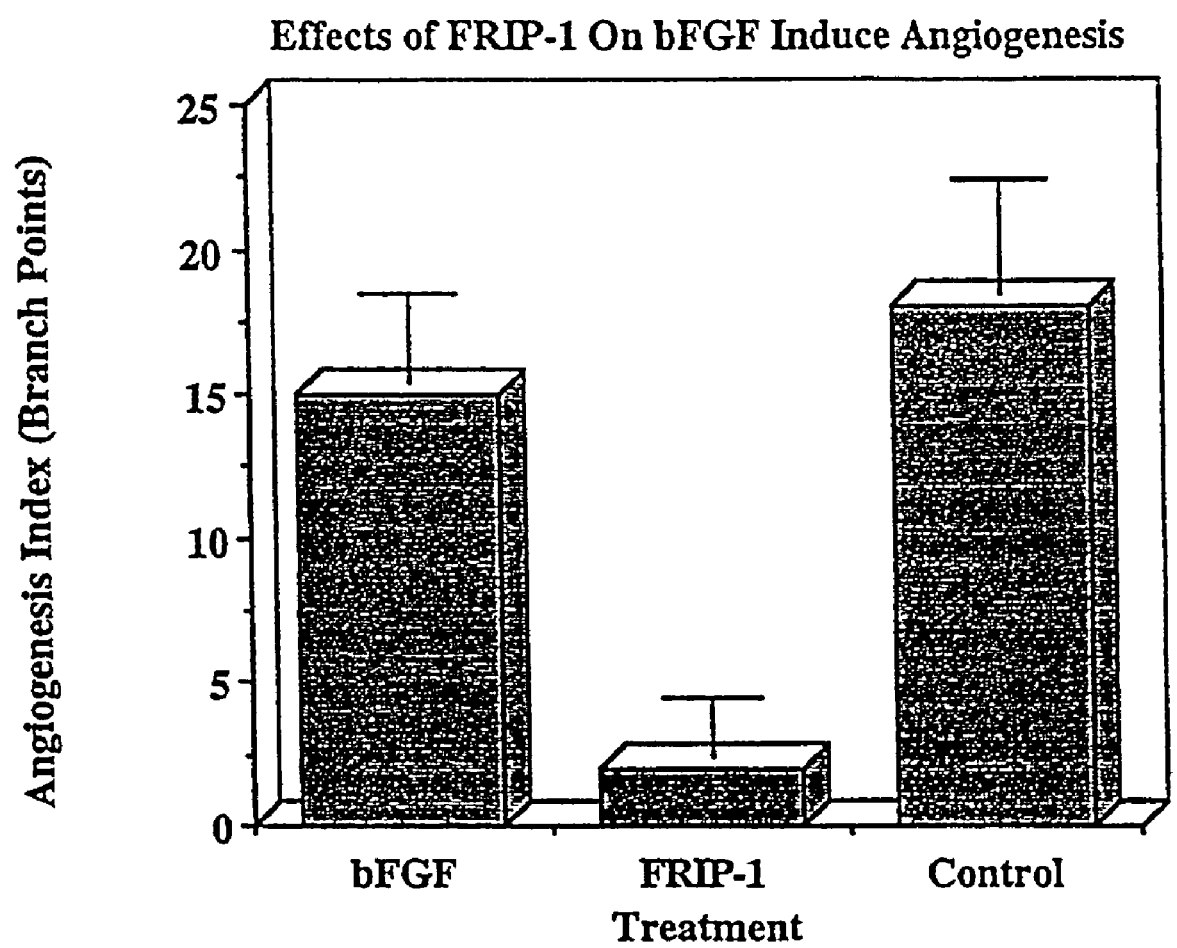

Angiogenesis was induced on the CAMs of 10 day old chick embryos with bFGF. Twenty-four hours later the embryos received a single IV injection with 100 μg of FRIP-1 or AAA control peptide. Three days later angiogenesis was quantified by counting the number of blood vessel branch points within the area of the filter disc. FIG. 8A shows representative examples of CAM tissue from a typical experiment. FIG. 8B is a quantification of the angiogenesis experiments. The results in FIG. 8B show that the FRIP-1 synthetic peptide that binds to MMP-9 blocks angiogenesis in the Chick Embryo CAM Model. In FIG. 8B, NT corresponds to No bFGF, FRIP-1 to bFGF+FRIP-1 peptide, and AAA to bFGF+control AAA peptide. Data bars represent the mean±standard errors of 5 to 10 embryos per condition.

This data suggests that MMP-9/α5β1 interaction may play an important role in angiogenesis.

Example 9

Generation of Mabs Directed to Synthetic Peptides

FRIP-1 peptide was conjugated to the carrier protein KLH and injected into mice. Conditioned medium from 5 representative hybridoma clones were analyzed by ELISA for binding to FRIP-1 peptide or control AAA peptide. The data, shown in FIG. 9, represents the mean relative binding (optical density)±standard deviation from triplicate wells.

A number of Mabs were generated, as shown in FIG. 9, to the FRIP-1 peptide and some of these antibodies, for example Mab FM155, showed high specificity to the FRIP-1 peptide but did not react with the control peptide AAA. Thus, Mab FM155 was chosen for further evaluation.

Example 10

Effects of Mab FM155 on MMP-9/α5β1 Interactions

Figure 10:
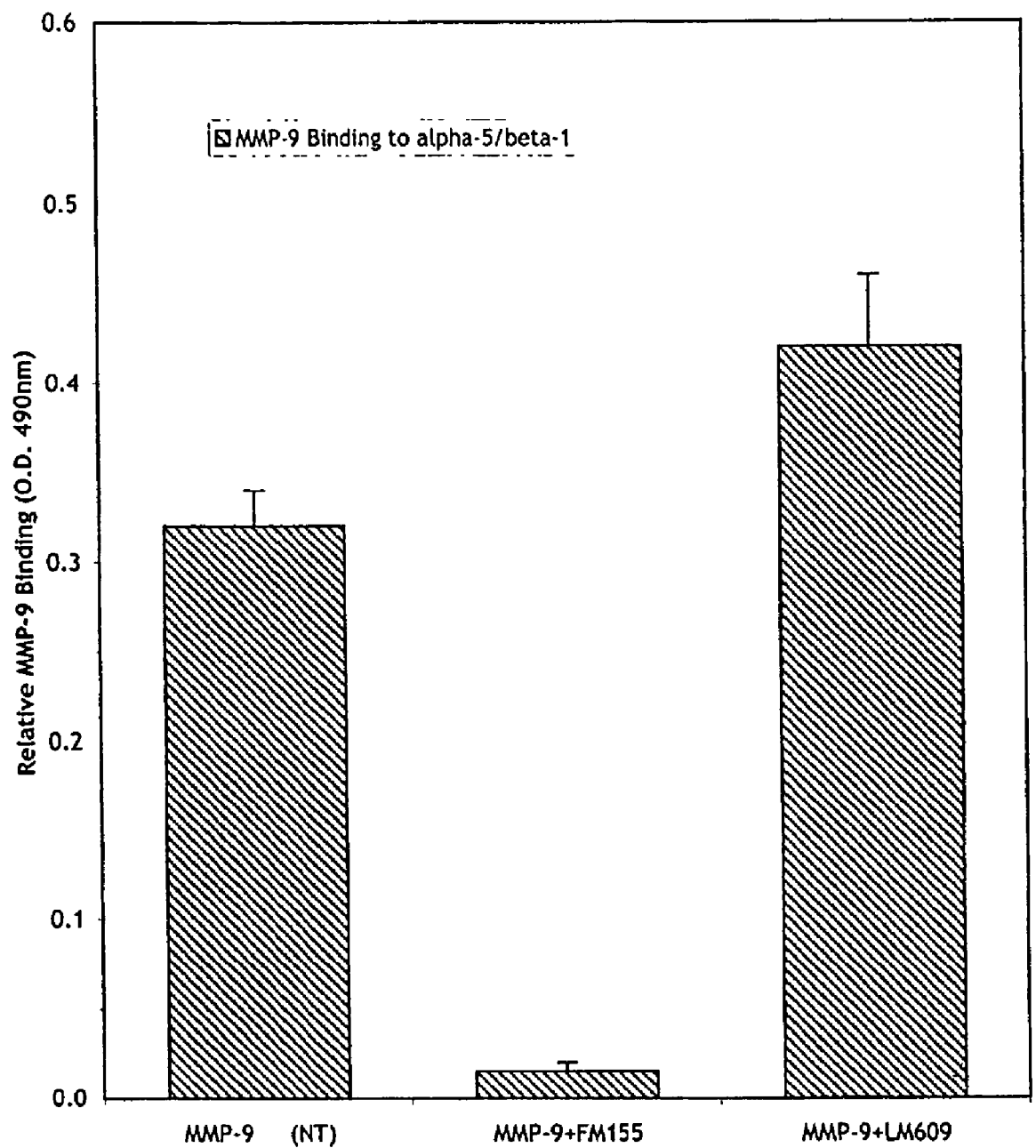
FIG. 10: Shows the results of experiments in which recombinant human MMP-9 (2 μg/ml) was allowed to bind in the presence or absence of Mabs FM155 or LM609.

Conclusions

α5β1 was immobilized on microtiter wells (10 μg/ml). Recombinant human MMP-9 (2 μg/ml) was allowed to bind in the presence or absence of Mabs FM155 or LM609. MMP-9 binding was detected with anti-MMP-9 polyclonal antibody. The results are shown in FIG. 10. Data bars represent the mean optical density ±standard deviations from triplicate wells. In the figure, NT corresponds to no treatment, FM155 to Mab anti-FRIP-1 and LM609 to anti-αvβ3 Mab.

FIG. 10 shows that Mab FM155 specifically blocked the ability of MMP-9 to bind to purified α5β1 suggesting that FM155 be used to disrupt this interaction in vivo.

Example 11

Effects of Systemic Administration of FM155 on Melanoma Tumor Growth

Figure 11:
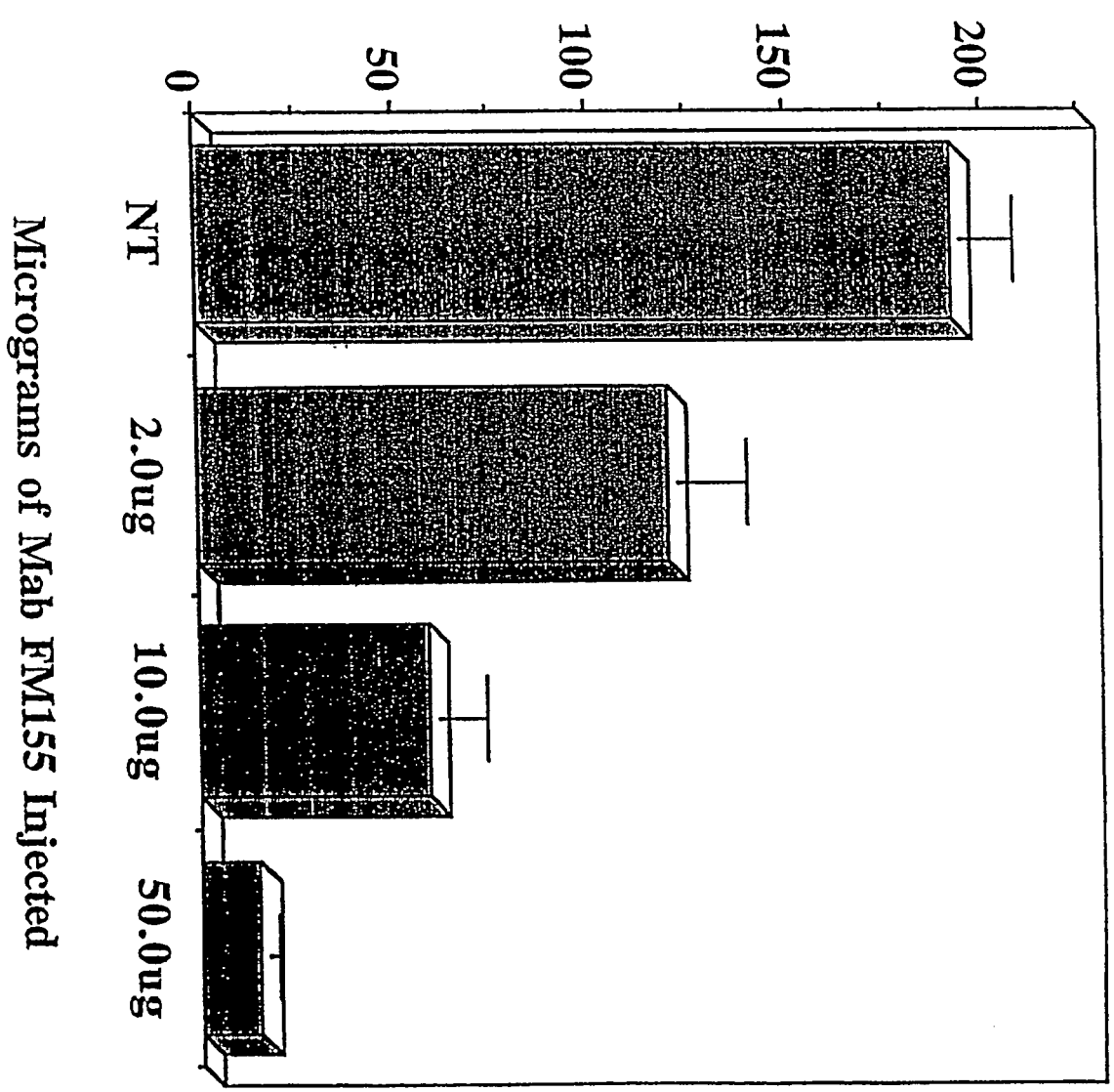
FIG. 11: Shows the results of experiments to determine the effects of systemic administration of FM155 on melanoma tumor growth.

CS-1 melanoma cells ($5 \times 10^6$) were inoculated on the CAMs of 10 day old chick embryos. Twenty-four hours later, the embryos received a single intravenous injection of purified Mab FM155 (2.O μg, 10.0 μg, 50.0 μg) After 7 days tumors were resected and wet weights determined. FIG. 11 presents the quantification of tumors' weight. Data bars represent the mean±the standard errors from 5 to 10 embryos per condition. NT represents data for no treatment.

FIG. 11 illustrates that Mab FM155 potently inhibits CS-1 melanoma tumor growth in vivo. These findings indicate that the blocking of the interactions of MMP-9 and α5β1 may play a significant role in regulating angiogenesis and tumor growth in vivo.

All of the following publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

What is claimed is:

1. An isolated antagonist that inhibits angiogenesis, tumor growth, or metastasis by modifying protein-protein interactions between MMP-9 and a β1-containing integrin, wherein the isolated antagonist comprises an antibody reagent which specifically hinds to a polypeptide comprising SEQ ID NO: 1.

2. The isolated antagonist of claim 1 wherein the β1-containing integrin is α5β1 integrin.

3. The isolated antagonist of claim 1 wherein the protein-protein interactions cause co-localization of matrix metalloproteinase 9 (MMP-9) and a β1-containing integrin on the cell surface of a blood vessel.

4. The isolated antagonist of claim 1 wherein said isolated antagonist is a monoclonal antibody.

5. The isolated antagonist of claim 1 wherein the isolated antagonist is a polyclonal antibody.

6. The isolated antagonist of claim 1 wherein the isolated antagonist is a humanized or chemically modified monoclonal antibody.

7. The isolated antagonist of claim 1 wherein the isolated antagonist is a fragment of a monoclonal antibody.

8. The isolated antagonist of claim 1 wherein the isolated antagonist is conjugated to cytotoxic or cytostatic agents.

9. A method of inhibiting angiogenesis in a tissue comprising administering the isolated antagonist of claim 1.

10. The method of claim 9 wherein said isolated antagonist is administered intravenously, transdermally, intrasynovially, intramuscularly, intratumorally, intraocularly, intranasally, intrathecally, topically or orally.

11. The method of claim 9 wherein said isolated antagonist is administered in conjunction with chemotherapy.

12. The method of claim 9 wherein said isolated antagonist is administered in conjunction with radiation.

13. The method of claim 9 wherein the tissue is inflamed and angiogenesis is occurring.

14. The method of claim 13 wherein the tissue is present in a mammal.

15. The method of claim 14 wherein the tissue is arthritic, ocular, retinal or a hemangioma.

16. A method of inhibiting tumor growth or metastasis in a tissue comprising administering the isolated antagonist of claim 1.

17. The method of claim 16 wherein said isolated antagonist is administered intravenously, transdermally, intrasynovially, intramuscularly, intratumorally, intraocularly, intranasally, topically or orally.

18. The method of claim 16 wherein said isolated antagonist is administered in conjunction with chemotherapy.

19. The method of claim 16 wherein said isolated antagonist is administered in conjunction with radiation.

20. The method of claim 16 wherein the tumor or metastasis is a melanoma, carcinoma, sarcoma, fibrosarcoma, glioma or astrocytoma.

21. A method of inhibiting psoriasis, macular degeneration, or restenosis in a tissue by administering the isolated antagonist of claim 1.

22. The method of claim 21 wherein said isolated antagonist is administered intravenously, transdermally, intrasynovially, intramuscularly, intratumorally, intraocularly, intranasally, intrathecally, topically or orally.

23. The method of claim 21 wherein administering the isolated antagonist is in conjunction with chemotherapy.

24. The method of claim 21 wherein administering the isolated antagonist is in conjunction with radiation.

* * * * *

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:

```
<223> OTHER INFORMATION: Synthetic sequence, FRIP-1
<220> FEATURE:
<223> OTHER INFORMATION: Binds to MMP-9 and beta 1 integrins.

<400> SEQUENCE: 1

Cys Arg Leu Arg Ser Gly Glu Pro Gln Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic sequence, AAA
<220> FEATURE:
<223> OTHER INFORMATION: Binds to MMP-9 and beta 1 integrins with
      substantially reduced binding capacity compared to
      the binding capacity of FRIP-1 to MMP-9 and beta 1
      integrins.

<400> SEQUENCE: 2

Cys Arg Ala Ala Ala Gly Glu Pro Gln Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic sequence, AAAA
<220> FEATURE:
<223> OTHER INFORMATION: Binds to MMP-9 and beta 1 integrins with
      substantially reduced binding capacity compared to
      the binding capacity of FRIP-1 to MMP-9 and beta 1
      integrins.

<400> SEQUENCE: 3

Cys Arg Ala Ala Ala Ala Glu Pro Gln Cys
1               5                   10
```